(12) United States Patent
Wang et al.

(10) Patent No.: US 11,612,885 B2
(45) Date of Patent: Mar. 28, 2023

(54) METHODS, COMPOSITIONS AND KITS USEFUL FOR PH GRADIENT CATION EXCHANGE CHROMATOGRAPHY

(71) Applicant: WATERS TECHNOLOGIES CORPORATION

(72) Inventors: Qi Wang, Belmont, MA (US); Matthew A. Lauber, North Smithfield, RI (US)

(73) Assignee: WATERS TECHNOLOGIES CORPORATION

( * ) Notice: Subject to any disclaimer, the term of this patent is extended or adjusted under 35 U.S.C. 154(b) by 994 days.

(21) Appl. No.: 16/406,816

(22) Filed: May 8, 2019

(65) Prior Publication Data
US 2019/0344256 A1   Nov. 14, 2019

Related U.S. Application Data

(60) Provisional application No. 62/668,748, filed on May 8, 2018.

(51) Int. Cl.
| | |
|---|---|
| *B01J 49/53* | (2017.01) |
| *B01J 39/05* | (2017.01) |
| *B01D 15/36* | (2006.01) |
| *B01J 39/18* | (2017.01) |
| *B01J 39/26* | (2006.01) |
| *B01J 47/02* | (2017.01) |
| *C07K 1/18* | (2006.01) |
| *C07K 16/24* | (2006.01) |
| *C07K 16/28* | (2006.01) |
| *C07K 16/32* | (2006.01) |
| *G01N 30/08* | (2006.01) |
| *B01J 47/022* | (2017.01) |

(52) U.S. Cl.
CPC .......... *B01J 49/53* (2017.01); *B01D 15/362* (2013.01); *B01J 39/05* (2017.01); *B01J 39/18* (2013.01); *B01J 39/26* (2013.01); *B01J 47/022* (2013.01); *C07K 1/18* (2013.01); *C07K 16/241* (2013.01); *C07K 16/2863* (2013.01); *C07K 16/32* (2013.01); *G01N 30/08* (2013.01); *G01N 2030/085* (2013.01)

(58) Field of Classification Search
CPC ... B01J 49/53; B01J 39/05; B01J 39/18; B01J 39/26; B01J 47/022; B01D 15/362; C07K 1/18; C07K 16/241; C07K 16/2863; C07K 16/32; G01N 30/08; G01N 2030/085
USPC ...................................................... 73/61.55
See application file for complete search history.

(56) References Cited

U.S. PATENT DOCUMENTS

| | | | |
|---|---|---|---|
| 4,530,956 A | 7/1985 | Ugelstad et al. | |
| 5,130,343 A | 7/1992 | Frechet et al. | |
| 5,292,818 A | 3/1994 | Oishi et al. | |
| 5,324,752 A | 6/1994 | Barretto | |
| 6,423,666 B1 | 7/2002 | Liao et al. | |
| 6,858,301 B2 | 2/2005 | Ganapathiappan | |
| 7,265,159 B2 | 9/2007 | Klipper et al. | |
| 7,540,962 B2 | 6/2009 | Biermans | |
| 8,921,113 B2 * | 12/2014 | Lin ........................ | C09K 15/30 435/7.1 |
| 2002/0155090 A1 | 10/2002 | Takahashi et al. | |
| 2003/0004094 A1 * | 1/2003 | Ghose ................... | B01D 15/16 530/416 |
| 2007/0193954 A1 | 8/2007 | Busson | |
| 2009/0148435 A1 * | 6/2009 | Lebreton ................ | A61P 19/02 530/416 |
| 2012/0024791 A1 | 2/2012 | Deetz et al. | |
| 2014/0179008 A1 * | 6/2014 | Lin ........................ | C09K 15/30 436/18 |
| 2014/0370614 A1 | 12/2014 | Liu et al. | |
| 2015/0285771 A1 | 10/2015 | Wang et al. | |

FOREIGN PATENT DOCUMENTS

| | | | | |
|---|---|---|---|---|
| EP | 2745902 A1 * | 6/2014 | .......... | B01D 15/168 |
| EP | 2745902 A1 | 6/2014 | | |
| WO | 8303920 A1 | 11/1983 | | |

OTHER PUBLICATIONS

Kroner et al. "Systematic generation of buffer systems for pH gradient ion exchange chromatography and their application", Journal of Chromatography A, 1285 (2013), pp. 78-87 (Year: 2013).*

Fekete, S., et al., "Method development for the separation of monclonal antibody charge variants in cation exchange chromatography. Part II: pH gradient approach", Journal of pharmaceutical and biomedical analysis, 102:282-9 (2015).

Erbay, E., and Okay, O., "Pore Memory of macroporous Styrene-Divinylbenzene Copolymers", J Appl. Poly Sci. 71:1055-1062 (1999).

Li, K., et al., "Synthesis of monodisperse poly(divinylbenzene) microspheres", J Polym. Sci Part A: Polym Chem 31:3257-3263 (1993). Abstract.

(Continued)

*Primary Examiner* — Michael M. Bernshteyn
(74) *Attorney, Agent, or Firm* — Womble Bond Dickinson (US) LLP; Deborah M. Vernon

(57) ABSTRACT

The present disclosure relates to methods, compositions and kits useful for the enhanced pH gradient cation exchange chromatography of a variety of analytes. In various aspects, the present disclosure pertains to chromatographic elution buffer solutions that comprise a first buffer salt, a second buffer salt, a third buffer salt, and fourth buffer salt. The first buffer salt may be, for example, a diprotic acid buffer salt, the second buffer salt may be, for example, a divalent buffer salt with two amine groups, the third buffer salt may be, for example, a monovalent buffer salt comprising a single amine group, and the fourth buffer salt may be, for example, a zwitterionic buffer salt. Moreover, the buffer solution has a pH ranging from 3 to 11.

25 Claims, 11 Drawing Sheets

(56) References Cited

OTHER PUBLICATIONS

Downey, J.S., et al., "Growth Mechanism of Poly(divinylbenzene) Microspheres in Precipitation Polymerization", Macromolecules 32:2838-2844 (1999).
Padhye, S., et al., "Transition metal complexes of semicarbazones and thiosemicarbazones", Can J. Chem, 63:127-160 (1985). Abstract.
Cao, M., et al., "Preparation of higihly crosslinked mondisperse poly(styrene-co-divinylbenzene) microspheres by two-stage dispersion polymerization", J. Appl. Polym Sci 109:1189-1196 (2008) Abstract.
Takekoh, R., et al., "Multilayered Polymer Microspheres by Thermal Imprinting during Microsphere Growth", J Am. Chem Soc. 128(1):240-244 (2006) Abstract.
Zhang, L., et al., "Improving pH gradient cation-exchange chromatography of monoclonal antibodies by controlling ionic strength", Journal of Chromatography A 1272:56-64 (2013) Abstract.
Kroner, F., and Hubbuch, J., "Systematic generation of buffer systems for pH gradient ion exchange chromatography and their application", Journal of Chromatography A 1285:78-87 (2013).
International Search Report and Written Opinion for International application No. PCT/US2019/031345, dated Aug. 5, 2019, 9 pages.
Kroner, F., et al., "Systematic generation of buffer systems for pH gradient ion exchange chromatography and their application", Journal of Chromatography A, 1285:78-87 (2013).
Author unknown, "Biological Buffers", AppliChem brochure [online], 2008 [retrieved on Apr. 7, 2020]. Retrieved from Internet URL: https://www.applichem.com/fileadmin/Broschueren/BioBuffer.pdf, 20 pages.
Fekete, S., et al., "Method development for the separation of monoclonal antibody charge variants in cation exchange chromatography. Part II: pH gradient approach", Journal of Pharmaceutical and Biomedical Analysis 102:282-9 (2015).

\* cited by examiner

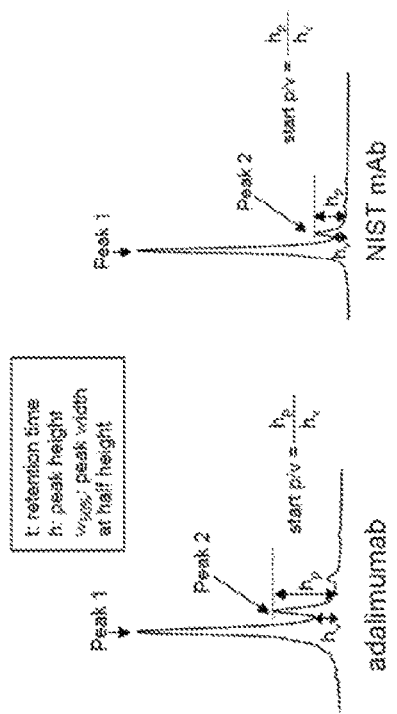
Fig. 1A infliximab
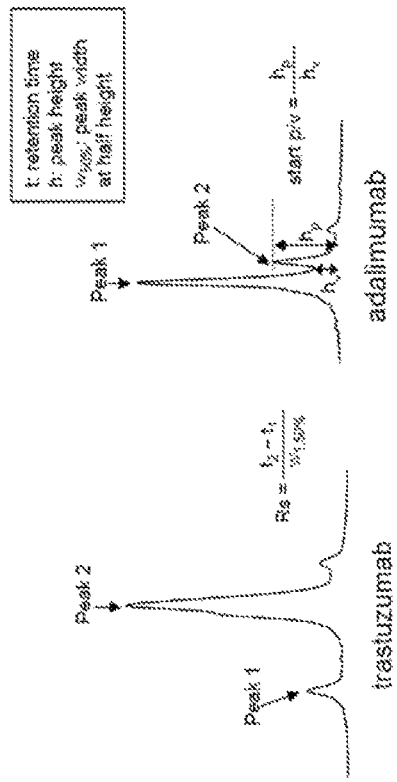
Fig. 1B trastuzumab
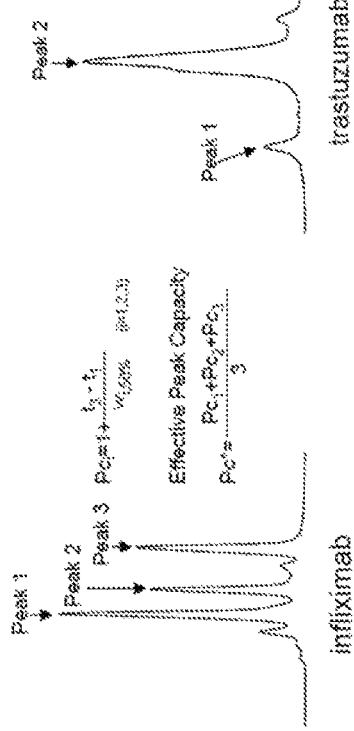
Fig. 1C adalimumab
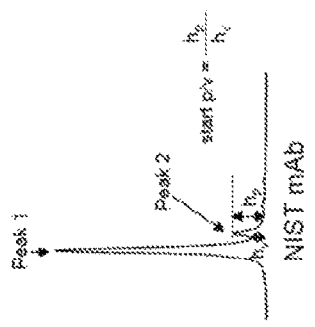
Fig. 1D NIST mAb
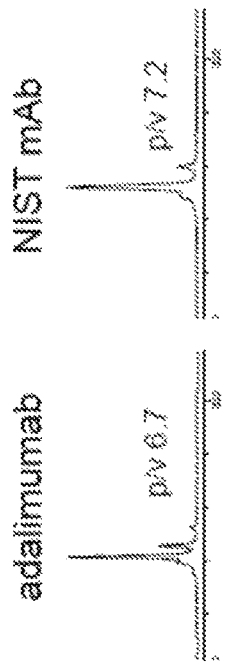
Fig. 2A
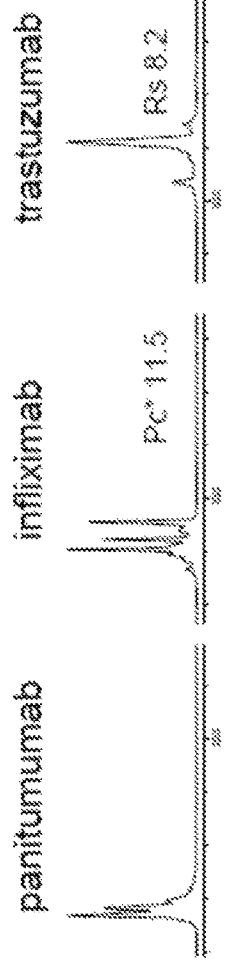
Fig. 2B panitumumab / infliximab / trastuzumab / adalimumab / NIST mAb

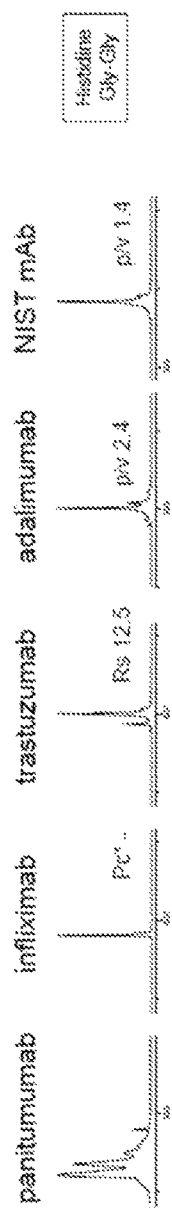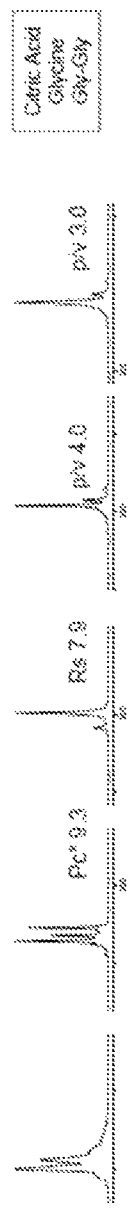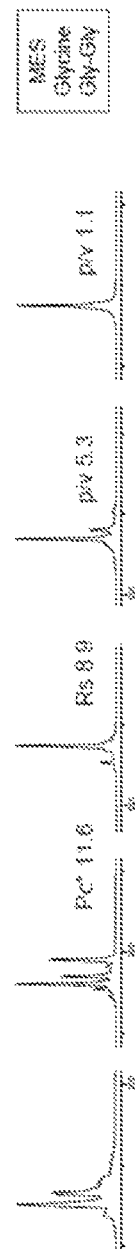
Fig. 3A
Fig. 3B
Fig. 3C
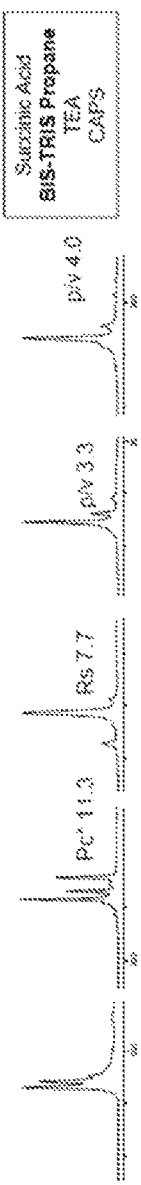
Fig. 4A
Fig. 4B

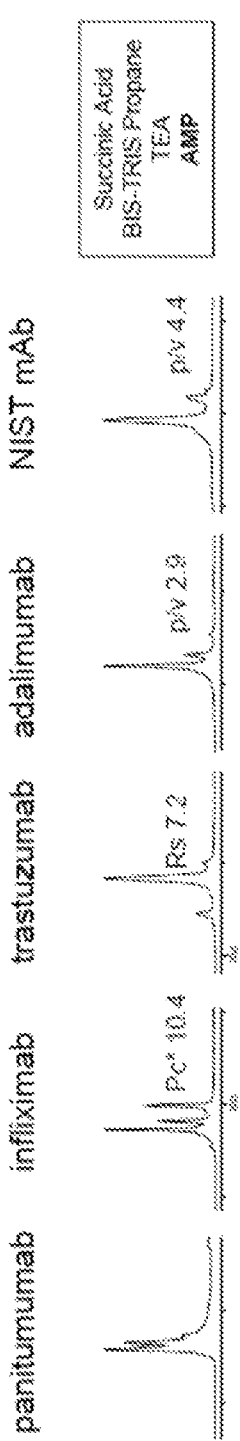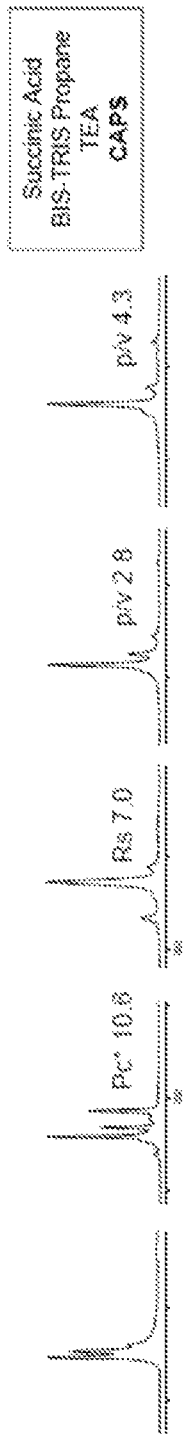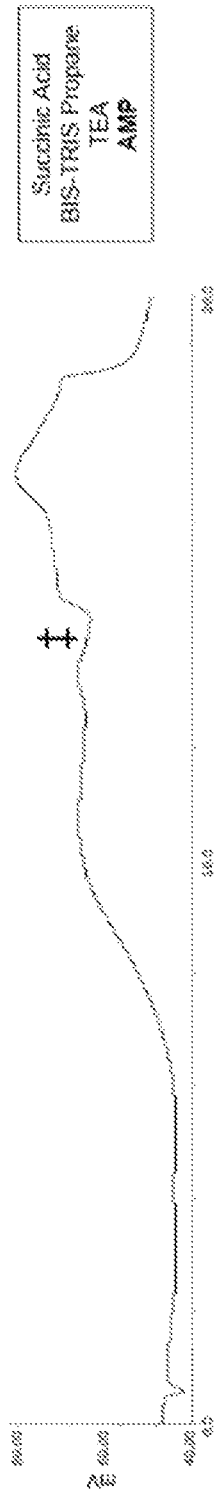
Fig. 5A
Fig. 5B
Fig. 5C

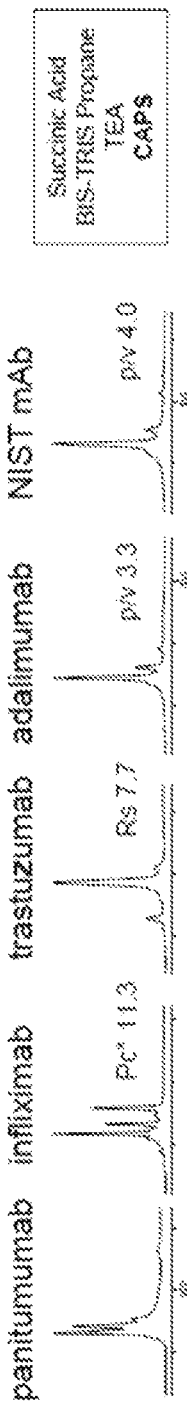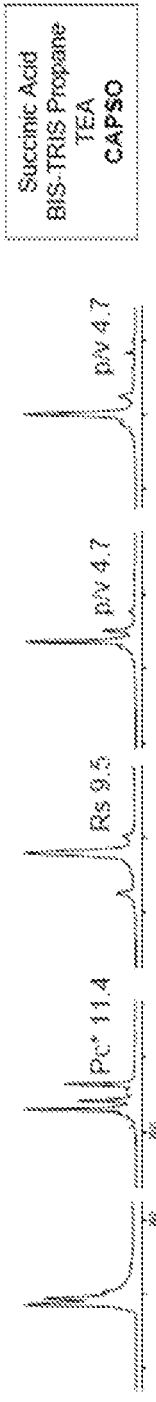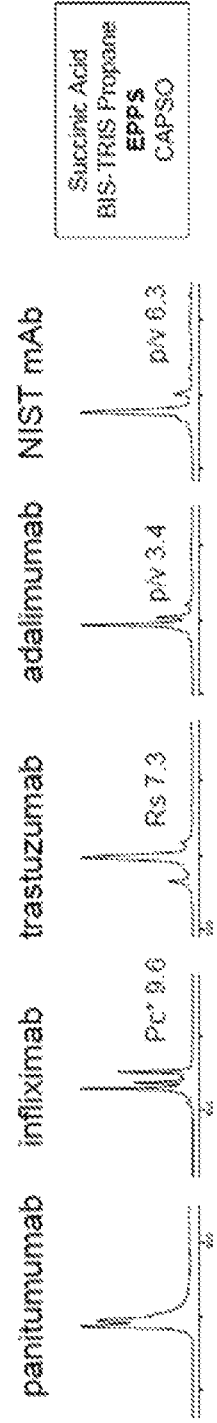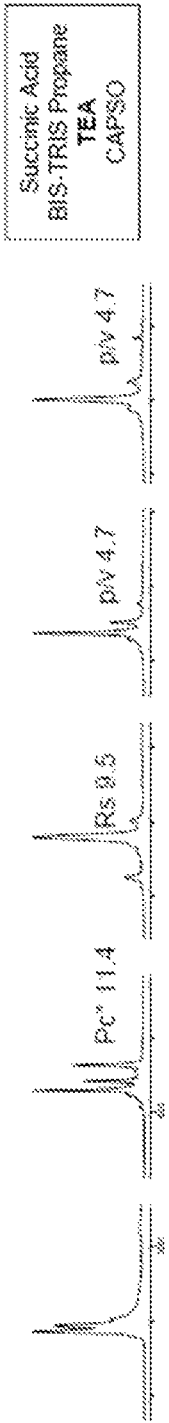
Fig. 6A
Fig. 6B
Fig. 7A
Fig. 7B

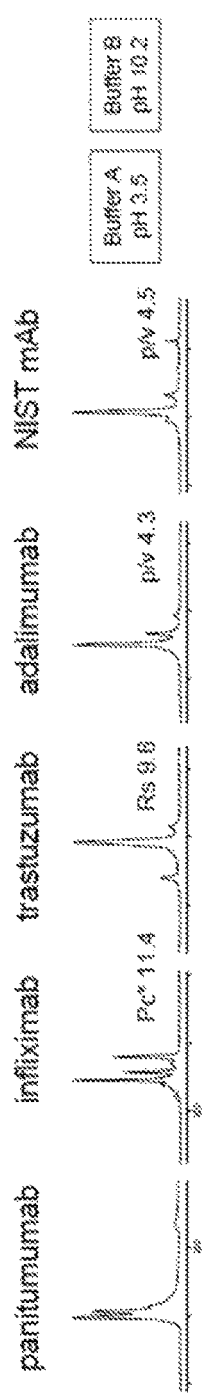 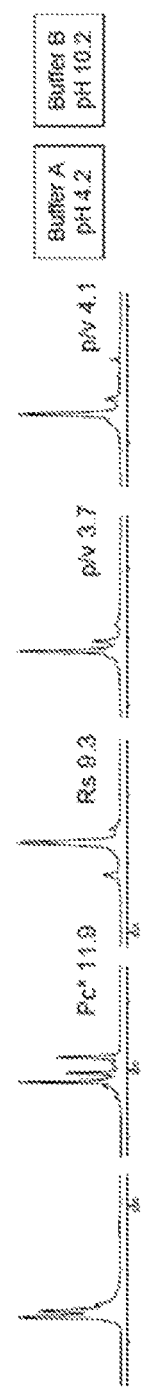 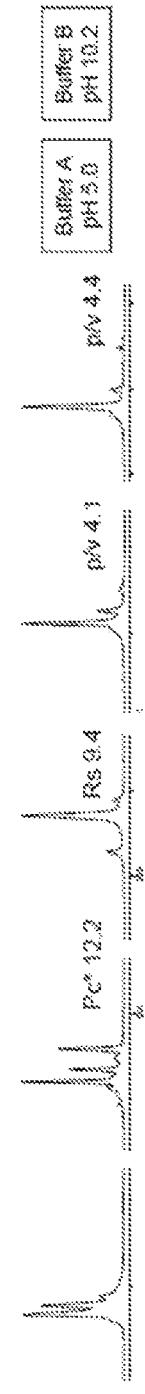 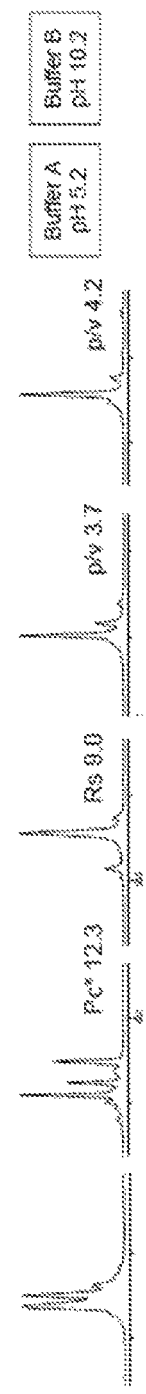 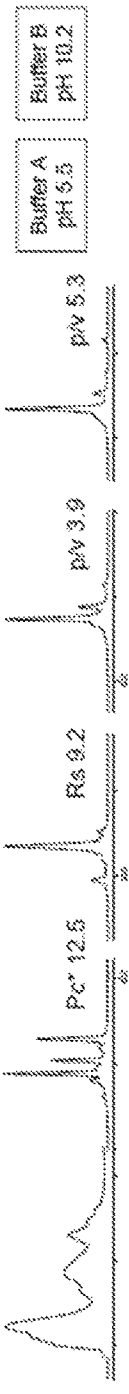
Fig. 11A
Fig. 11B
Fig. 11C
Fig. 11D
Fig. 11E

Fig. 12A
Fig. 12B
Fig. 12 C
Fig. 12D
Fig. 12E
Fig. 12F
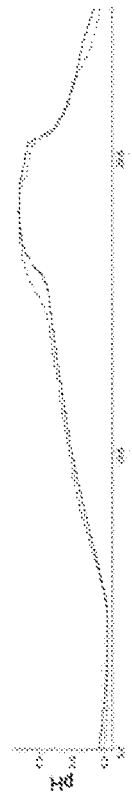
Fig. 12G
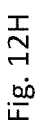
Fig. 12H

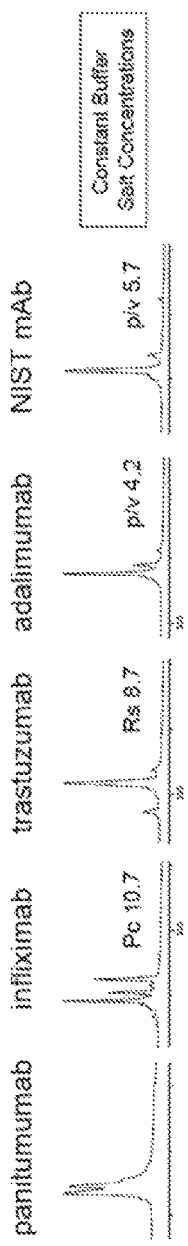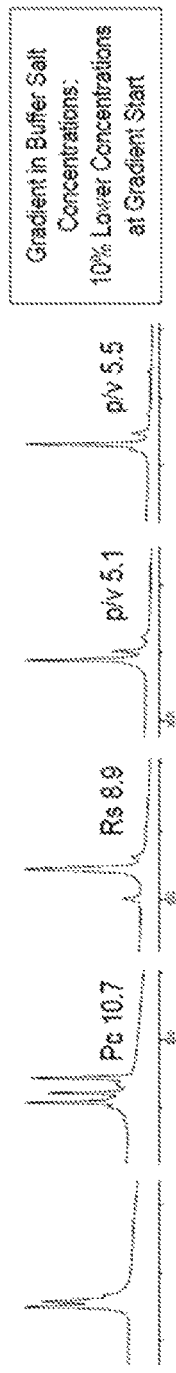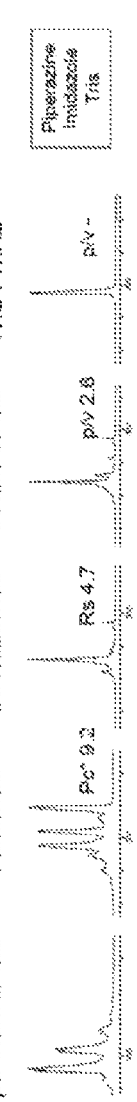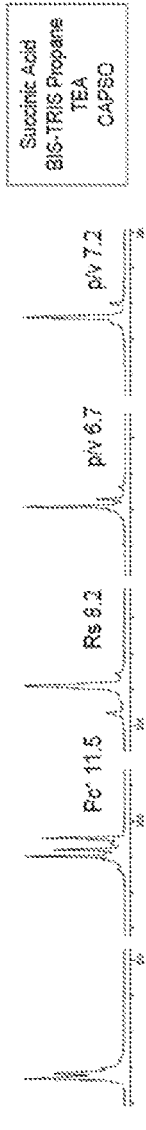
Fig. 14A
Fig. 14B
Fig. 15A
Fig. 15B
Fig. 15C

METHODS, COMPOSITIONS AND KITS USEFUL FOR PH GRADIENT CATION EXCHANGE CHROMATOGRAPHY

CROSS-REFERENCE TO RELATED APPLICATIONS

This application claims the benefit of U.S. Provisional Application Ser. No. 62/668,748, filed May 8, 2018, which is incorporated herein by reference in its entirety.

FIELD

The present disclosure relates to methods, compositions and kits useful for the enhanced pH gradient cation exchange chromatography of a variety of analytes.

BACKGROUND

Monoclonal antibodies (mAbs) represent a very important type of protein therapeutic in the fast-growing biotechnology industry. They have been applied to the treatment of multiple diseases and have accordingly been proven to be important modalities for various types of therapies. Nevertheless, their heterogeneity poses an analytical challenge. mAbs are subject to a range of different post-translational modifications that are an intrinsic outcome of their recombinant expression. Their modifications need to be carefully characterized since minor structural changes of mAbs can have a significant impact on properties, including stability, potency, and efficacy. Some of their modifications cause a change to their net charge. For example, deamidation and sialylation generate acidic variants whereas C-terminal lysine variation results in the presence of basic variants.

Using ion exchange chromatography, it is possible to learn about these protein variants. In ion exchange, charged molecules are separated based on their ionic interactions with an oppositely charged stationary phase. This technique can be applied to protein separations upon considering that all proteins have an isoelectric point (pI), which is defined as the pH at which a protein carries a net neutral charge. Below this value, a protein is positively charged. Above this value, the protein is negatively charged. Thus, under a condition where pH<pI, proteins will adsorb to a negatively charged stationary phase, like that found in a cation exchange column.

A protein can be made to elute from a cation exchanger via various mechanisms, including a salt gradient separation and a pH gradient separation. In a salt gradient separation, more highly charged proteins require increasingly higher concentrations of salt (NaCl, KCl, etc.) to be eluted from the stationary phase. In contrast, in a pH gradient technique, proteins with different pIs can be separated through a change in their own net charge as influenced by a change in mobile phase pH. By affecting protein net charge, the change in mobile phase pH can cause the protein to exhibit an increasingly weaker Coulombic attraction with an ion exchange stationary phase. Salt gradient separations have been quite common for charge variant profiling. However, various factors in a salt gradient method, including the choice of buffer salts, ionic strengths of buffer salts, and buffer pH, need to be optimized for each individual sample. On the other hand, a well-developed pH gradient technique has the promise of being applicable to many different samples, in what is sometimes referred to as a 'platform method'. Unfortunately, it is rather challenging to develop a pH gradient method that exhibits both robustness and the capability to yield high resolution separations over a wide pH range.

In this regard, Zhang et al. previously developed a so-called "salt-mediated pH gradient method" based on the buffer salts piperazine, imidazole, and Tris (2-amino-2-(hydroxymethyl)propane-1,3-diol), and a non-buffer salt, sodium chloride. The ionic strength of the sodium chloride was optimized to ensure a relatively constant conductivity throughout the applied pH gradient. This method was optimized for a weak cation exchange stationary phase using a long gradient, and it was shown to provide reproducible separations for mAbs over the pI range of 6.2 to 9.4. However, the present inventors have found the resolution of medium to high pI mAbs to be non-ideal when short gradients were used with a non-porous sulfonated strong cation exchange stationary phase. Furthermore, piperazine is known to cause acute respiratory and skin irritation as well as organ damage with prolonged exposure.

More recently, Thermo Fisher Scientific developed a pH gradient buffer kit (the CX-1 pH Gradient Buffer Kit;) based on four zwitterionic buffer salts having both sulfonate and amine groups. This buffer kit provides a linear pH curve over the range of 5.6 to 10.2 and a linear conductivity trace mediated by a non-buffer salt. This buffer kit has been found to provide good resolution for mAbs with low to medium pI values, but has insufficient resolution for mAbs with high pI values.

SUMMARY

The present disclosure provides novel methods, mobile phase compositions, and kits to facilitate pH gradient cation exchange chromatography of analytes while providing enhanced peak resolution and reproducibility.

In various aspects, the present disclosure pertains to chromatographic elution buffer solutions that comprise a first buffer salt, a second buffer salt, a third buffer salt and fourth buffer salt. In embodiments pertaining to these aspects, (a) the first buffer salt may be, for example, a diprotic acid buffer salt, (b) the second buffer salt may be, for example, a divalent buffer salt with two amine groups, (c) the third buffer salt may be, for example, a monovalent buffer salt comprising a single amine group, and (d) the fourth buffer salt may be, for example, a zwitterionic buffer salt. Moreover, the buffer solution has a pH ranging from 3 to 11.

In various aspects, the present disclosure pertains to chromatographic elution buffer solutions that comprise (a) a first buffer salt comprising a first pKa value, (b) a second buffer salt comprising a second pKa value, (c) a third buffer salt comprising a third pKa value, and (d) a fourth buffer salt comprising a fourth pKa value, wherein the first pKa value is less than the second pKa value, the second pKa value is less than the third pKa value, and the third pKa value is less than the fourth pKa value, and wherein the buffer solution has a pH ranging from 3 to 11. The first pKa value may differ from the second pKa value, for example, by a first amount ranging from 0.2-2.0, more typically by a first amount ranging from 0.4-1.6, even more typically by a first amount ranging from 0.5 to 1.4. The second pKa value may differ from the third pKa value, for example, by a second amount ranging from 0.2-2.0, more typically by a second amount ranging from 0.4-1.6, even more typically by a second amount ranging from 0.5 to 1.4. The third pKa value may differ from the fourth pKa value, for example, by a third amount ranging from 0.2-2.0, more typically by a third amount ranging from 0.4-1.6, even more typically by a third amount ranging from 0.5 to 1.4. In embodiments pertaining to these aspects, the first pKa value may range, for example, from 3 to 5, the second pKa value may range, for example, from 5 to 7, the third pKa value may range, for example, from 7 to 9, and the fourth pKa value may range from 9 to 11. In embodiments pertaining to these aspects, the first buffer salt may be, for example, a diprotic acid buffer salt, (b) the second buffer salt may be, for example, a divalent buffer salt with two amine groups, (c) the third buffer salt may be, for example, a monovalent buffer salt comprising a single amine group, and (d) the fourth buffer salt may be, for example, a zwitterionic buffer salt.

In various aspects, the present disclosure pertains to chromatographic elution buffer solutions that comprise a plurality of buffer salts, the buffer solution having a first pKa value that ranges from 4.5 to 6.5, a second pKa value that ranges from 6.5 to 7.5, a third pKa value that ranges from 7.5 to 8.5, a fourth pKa value that ranges from 8.5 to 9.5, and a fifth pKa value that ranges from 9.5 to 11. In embodiments pertaining to these aspects, the first pKa value may be provided, for example, by a first buffer salt that is a diprotic acid buffer salt, (b) the second pKa value and the fourth pKa value may be provided, for example, by a second buffer salt that is a divalent buffer salt with two amine groups, (c) the third pKa may be provided, for example, by a third buffer salt that is a monovalent buffer salt comprising a single amine group, and (d) the fifth pKa value may be provided, for example, by a forth buffer salt that is a zwitterionic buffer salt.

In various embodiments, which may be used in conjunction with any of the preceding aspects and embodiments, the diprotic acid buffer salt may be, for example, succinic acid, maleic acid and malic acid.

In various embodiments, which may be used in conjunction with any of the preceding aspects and embodiments, the divalent buffer salt may be, for example, BIS-TRIS propane.

In various embodiments, which may be used in conjunction with any of the preceding aspects and embodiments, the monovalent buffer salt may be, for example, selected from triethanolamine, BIS-TRIS (bis(2-hydroxyethyl)amino-tris (hydroxymethyl)methane), and TRIS.

In various embodiments, which may be used in conjunction with any of the preceding aspects and embodiments, the zwitterionic buffer salt may be, for example, selected from zwitterionic buffer salt comprising a sulfonate group and an amine group and a zwitterionic buffer salt comprising a carboxyl group and an amine group.

In various embodiments, which may be used in conjunction with any of the preceding aspects and embodiments, the zwitterionic buffer salt may be, for example, selected from CAPSO, CAPS, β-alanine, and other β-amino acids.

In various aspects, the present disclosure pertains to chromatographic elution buffer kits that (a) a first buffer solution comprising a chromatographic elution buffer in accordance with any of the preceding aspects and embodiments having a first pH and (b) a second buffer solution comprising a chromatographic elution buffer in accordance with any of the preceding aspects and embodiments and further comprising a non-buffer salt, the second buffer solution having a second pH that is higher than the first p. The first buffer solution may have a pH ranging from 3 to 7, typically from 3.5 to 5.5 (e.g., in the case of a ready-to-use buffer solution) or, in the case where a buffer concentrate is provided, the first buffer solution may have a pH ranging from 3 to 7, typically from 3.5 to 5.5, upon dilution with a suitable dilution fluid (e.g., distilled water, deionized water, etc.), for instance, in a ratio ranging from 1:2 to 1:20, more typically ranging from 1:5 to 1:15, even more typically ranging from about 1:10. The second buffer solution, on the other hand, may have a pH ranging from 9 to 11, typically from 9.5 to 10.7 (e.g., in the case of a ready-to-use buffer solution) or, in the case where a buffer concentrate is provided, the second buffer solution may have a pH ranging from 9 to 11, typically from 9.5 to 10.7, upon dilution with suitable dilution fluid (e.g., distilled water, deionized water, etc.), for instance, in a ratio ranging from 1:2 to 1:20, typically from 1:5 to 1:15, more typically about 1:10.

In various embodiments, the non-buffer salt may comprise, for example, (a) a cation selected from alkali metal cations, alkaline earth metal cations, transition metal cations, ammonium cations and (b) an anion selected from selected from halide anions, nitrate anions, sulfate anions, phosphate anions, carbonate anions, chlorate anions, thiocyanate anions and perchlorate anions. In various embodiments, the non-buffer salt may be NaCl and/or KCl. Moreover, the concentration of the non-buffer salt may range, for example, from 1 to 100 millimolar, typically ranging from 5 to 60 millimolar.

In various embodiments, which may be used in conjunction with any of the preceding aspects and embodiments, the first and second buffer solutions may contain less than 100 ppm concentrations of heavy metals, including but not limited to iron.

In various embodiments, which may be used in conjunction with any of the preceding aspects and embodiments, in order to lengthen shelf life, the first and second buffer solutions may be formulated with a trace amount of bactericidal agent, including by not limited to approximately 200 ppm of chloroform, and packaged with an oxygen absorbing packet.

In various embodiments, which may be used in conjunction with any of the preceding aspects and embodiments, (a) each of the first buffer salt, second buffer salt, third buffer salt and fourth buffer salt (e.g., each of a diprotic acid buffer salt, a divalent buffer salt, a monovalent buffer salt and a zwitterionic buffer salt) may be present in the first buffer solution, for example, in a concentration ranging from 2 to 20 millimolar, typically ranging from 5 to 15 millimolar, more typically ranging from 8 to 11 millimolar, (b) each of the first buffer salt, second buffer salt, third buffer salt and fourth buffer salt (e.g., each of a diprotic acid buffer salt, a divalent buffer salt, a monovalent buffer salt and a zwitterionic buffer salt) may be present in the second buffer solution, for example, in a concentration ranging from 2 to 20 millimolar, typically ranging from 5 to 15 millimolar, more typically ranging from 8 to 11 millimolar, or (c) both (a) and (b).

In various embodiments, which may be used in conjunction with any of the preceding aspects and embodiments, a concentration of each of the first buffer salt, second buffer salt, third buffer salt and fourth buffer salt in the first buffer solution may be, for example, from 10% to 30% lower than a concentration of each of the first buffer salt, second buffer salt, third buffer salt and fourth buffer salt in the second buffer solution.

In various embodiments, which may be used in conjunction with any of the preceding aspects and embodiments, a total concentration of all of the first, second, third and fourth buffer salts in the first buffer solution may be, for example, from 10% to 30% lower than a total concentration of all of the first, second, third and fourth buffer salts in the second buffer solution.

In various embodiments, which may be used in conjunction with any of the preceding aspects and embodiments, a plot of (a) pH versus (b) volume percent of the first buffer solution (relative to a total volume for a binary mixture of the first buffer solution and the second buffer solution) is linear. As used herein, a plot of one variable versus another variable is "linear" when a linear least squares regression analysis yields a coefficient of determination (R2) value of at least 0.90, more typically 0.95.

In various embodiments, which may be used in conjunction with any of the preceding aspects and embodiments, a plot of (a) conductivity versus (b) volume percent of the first buffer solution (relative to a total volume for a binary mixture of the first buffer solution and the second buffer solution) is linear.

In various embodiments, which may be used in conjunction with any of the preceding aspects and embodiments, a plot of (a) conductivity versus (b) volume percent of the first buffer solution (relative to a total volume for a binary mixture of the first buffer solution and the second buffer solution) does not exhibit a negative slope.

In various embodiments, which may be used in conjunction with any of the preceding aspects and embodiments, the first buffer solution may have a conductivity ranging from 0.5 millisiemins (mS) to 3 mS, and the second buffer solution may have a conductivity ranging from 3 mS to 100 mS.

In various embodiments, which may be used in conjunction with any of the preceding aspects and embodiments, the chromatographic elution buffer kit further comprises an ion-exchange chromatography material. In these embodiments, the chromatographic elution buffer kit may include a separation device comprising a housing comprising an inlet and an outlet (e.g., a column, sample preparation device, centrifugation/spin column or microelution plate) that is configured to accept and hold the ion-exchange chromatography material. The ion-exchange chromatography material may be a cation exchange chromatography material, for instance, a cation exchange chromatography material comprising carboxylate groups and/or sulfonate groups.

In various aspects, the present disclosure pertains to methods for analyzing samples that that comprise a plurality of analytes, the methods comprising: loading the sample onto an ion-exchange chromatography material (e.g., a cation exchange chromatography material such as a cation exchange chromatography material comprising carboxy late groups and/or sulfonate groups), thereby binding the plurality of analytes to the ion-exchange chromatography material and eluting the plurality of analytes from the ion-exchange chromatography material with a mobile phase that comprises a chromatographic elution buffer in accordance with any of the above aspects and embodiments, thereby separating at least some of the plurality of analytes.

In various embodiments, which may be used in conjunction with the preceding aspects and embodiments, eluting the plurality of analytes from the ion-exchange chromatography material with the mobile phase comprises a course of elution in which a pH of the mobile phase is altered over time, in which an ionic strength of the mobile phase is altered over time, or both.

In various embodiments, which may be used in conjunction with any of the preceding aspects and embodiments, eluting the plurality of analytes from the ion-exchange chromatography material with the mobile phase comprises a course of elution in which a pH of the mobile phase is increased over time, in which an ionic strength of the mobile phase is increased over time, or both.

In embodiments where the pH of the mobile phase is increased during the course of elution, the pH of the mobile phase may be increased from 5.0 to 11.0, more typically from 5.0 to 10.2, during the course of elution. There may be, for example, a linear increase in the pH of the mobile phase during the course of elution.

In embodiments where the ionic strength of the mobile phase may be, for example, increased during the course of elution, there may be, for example, a linear increase in the ionic strength of the mobile phase during the course of elution.

In various embodiments, which may be used in conjunction with any of the preceding aspects and embodiments, a conductivity of the mobile phase is increased during the course of elution. In these embodiments, (a) the conductivity of the mobile phase may be increased between 1.5-fold and 10-fold, more typically between 2-fold and 5-fold, during the course of elution, (b) the conductivity of the mobile phase may be increased from a first value between 0.5 and 3 mS to a second value between 3 mS and 100 mS during the course of elution, or (c) both (a) and (b). In certain of these embodiments, there may be, for example, a linear increase in the conductivity during the course of elution.

In various embodiments, which may be used in conjunction with any of the preceding aspects and embodiments, a concentration of each of the first, second, third and fourth buffer salts in the mobile phase may increase between 10% and 40% during the course of elution.

In various embodiments, which may be used in conjunction with any of the preceding aspects and embodiments, a total concentration of all of the first, second, third and fourth buffer salts in the mobile phase may increase between 10% to 45% during the course of elution.

In various embodiments, which may be used in conjunction with any of the preceding aspects and embodiments, an automated system may be, for example, used to mix two, three, four or more solutions to form the mobile phase.

In various embodiments, which may be used in conjunction with any of the preceding aspects and embodiments, during at least a portion of the course of elution, the mobile phase comprises a non-buffer salt. In such embodiments, the course of elution may comprise a period during which a concentration of the non-buffer salt increases over time.

In various embodiments, which may be used in conjunction with any of the preceding aspects and embodiments, during the course of elution, the mobile phase may be formed from a buffer mixture that comprises (a) a first buffer solution comprising the first, second, third and fourth buffer salts, the first buffer solution having a pH ranging from 3 to 7 and (b) a second buffer solution comprising the first, second, third and fourth buffer salts and further comprising the non-buffer salt, the second buffer solution having a pH ranging from 9 to 11.

In these embodiments, the buffer mixture may comprise a binary mixture of the first buffer solution and the second buffer solution. Moreover, during the course of elution, a first volume percent of the first buffer solution in the buffer mixture may be decreased over time while at the same time increasing a second volume percent of the second buffer solution over time (also referred to herein as a concentration gradient separation), in which case the first volume percent in the buffer mixture may decrease linearly over time and the second volume percent in the buffer mixture may increase linearly during the course of elution, among other possibilities.

In various embodiments, which may be used in conjunction with any of the preceding aspects and embodiments, the sample material may be selected from biomolecular analytes, including but not limited to proteins, monoclonal antibodies, and fusion proteins.

In various embodiments, which may be used in conjunction with any of the preceding aspects and embodiments, the method may further comprise detecting the plurality of analytes.

In various embodiments, which may be used in conjunction with any of the preceding aspects and embodiments, the plurality of analytes in the sample may comprise a plurality of biomolecules.

In various embodiments, which may be used in conjunction with any of the preceding aspects and embodiments, the plurality of analytes may comprise a plurality of peptides or a plurality of proteins, including a plurality of mAb proteins, a plurality of non-mAb proteins, a plurality of fusion proteins, a plurality of antibody-drug conjugates (ADCs), and so forth.

DESCRIPTION OF THE DRAWINGS

FIGS. 1A-1D show exemplary ion exchange chromatograms and analysis of resolving power for charge variant profiling of infliximab (FIG. 1A), trastuzumab (FIG. 1B), adalimumab (FIG. 1C), and NIST mAb reference material 8671 (FIG. 1D). Calculation of effective peak capacity for infliximab (A), a pseudo resolution value using the acidic variant peak and the main peak for trastuzumab (FIG. 1B), and peak-to-valley ratios of the first lysine variant for adalimumab (FIG. 1C) and NIST mAb (FIG. 1C) are illustrated.

FIGS. 2A-2B show UV chromatograms (FIG. 2B) resulting from the use of a binary pH gradient buffer system (FIG. 2A) with a 3 μm non-porous sulfonated cation exchange stationary phase in a 4.6×50 mm column dimension. Charge variant separations are obtained for panitumumab, infliximab, trastuzumab, adalimumab, and NIST mAb reference material 8671.

FIGS. 3A-3C show ion exchange chromatograms of panitumumab, infliximab, trastuzumab, adalimumab, and NIST mAb reference material 8671 obtained using buffers composed of histidine and Gly-Gly (FIG. 3A), citric acid, glycine, and Gly-Gly (FIG. 3B), or MES, glycine, and Gly-Gly (FIG. 3C).

FIGS. 4A-4B show ion exchange chromatograms of panitumumab, infliximab, trastuzumab, adalimumab, and NIST mAb reference material 8671 obtained using buffers composed of succinic acid, ACES, 2-Amino-2-methyl-1,3-propanediol (AMPD), TEA, and CAPS (FIG. 4A) or succinic acid, BIS-TRIS propane, TEA, and CAPS (FIG. 4B).

FIGS. 5A-5B show ion exchange chromatograms of panitumumab, infliximab, trastuzumab, adalimumab, and NIST mAb reference material 8671 obtained using buffers composed of succinic acid, BIS-TRIS propane, TEA, and AMP (FIG. 5A) or succinic acid, BIS-TRIS propane, TEA, and CAPS (FIG. 5B). FIG. 5C shows conductivity traces observed using buffers composed of succinic acid, BIS-TRIS propane, TEA, and AMP.

FIGS. 6A-6B show ion exchange chromatograms of panitumumab, infliximab, trastuzumab, adalimumab, and NIST mAb reference material 8671 obtained using buffers composed of succinic acid, BIS-TRIS propane, TEA, and CAPS (FIG. 6A), or succinic acid, BIS-TRIS propane, TEA, and CAPSO (FIG. 6).

FIGS. 7A-7B show ion exchange chromatograms of panitumumab, infliximab, trastuzumab, adalimumab, and NIST mAb reference material 8671 obtained using buffers composed of succinic acid, BIS-TRIS propane, EPPS, and CAPSO (FIG. 7A) or (B) succinic acid, BIS-TRIS propane, TEA, and CAPSO (FIG. 7B).

FIGS. 11A-11E show ion exchange chromatograms of panitumumab, infliximab, trastuzumab, adalimumab, and NIST mAb reference material 8671 obtained using buffers composed of succinic acid, BIS-TRIS propane, TEA, and CAPSO when the pH values of the A buffers were titrated to 3.5 (FIG. 11A), 4.2 (FIG. 11B), 5.0 (FIG. 11C), 5.2 (FIG. 11D), or 5.5 (FIG. 11E) while keeping the pH of buffer B at 10.2.

FIG. 12A shows composition details for the pH gradient buffers b-h. FIGS. 12B-12H show pH traces obtained using buffer b (FIG. 12B), buffer c (FIG. 12C), buffer d (FIG. 12D), buffer e (FIG. 12E), buffer f (FIG. 12F), buffer g (FIG. 12G), and buffer h (FIG. 12H) (dashed traces) overlaid with buffer a (solid traces).

FIGS. 13A-13H show pH traces obtained using buffer a (FIG. 13A), buffer b (FIG. 13B), buffer c (FIG. 13C), buffer d (FIG. 13D), buffer e (FIG. 13E), buffer f (FIG. 13F), buffer g (FIG. 13G), and buffer h (FIG. 13H).

FIGS. 14A-14B show exchange chromatograms of panitumumab, infliximab, trastuzumab, adalimumab, and NIST mAb reference material 8671 obtained using buffers composed of succinic acid, BIS-TRIS propane, TEA, and CAPSO with the buffer compositions described as buffer h in FIG. 12A (FIG. 14A) and with a gradient of the buffer salt concentrations starting with 10% lower values in mobile phase A (versus mobile phase B) (FIG. 14B).

FIGS. 15A-15C show ion exchange chromatograms of panitumumab, infliximab, trastuzumab, adalimumab, and NIST mAb reference material 8671 obtained using buffers comprised of piperazine, imidazole, and Tris (FIG. 15A), Thermo Scientific CX-1 Buffer Kit (FIG. 15B), or succinic acid, BIS-TRIS propane, TEA, and CAPSO (FIG. 15C).

DETAILED DESCRIPTION

Figure 8A:
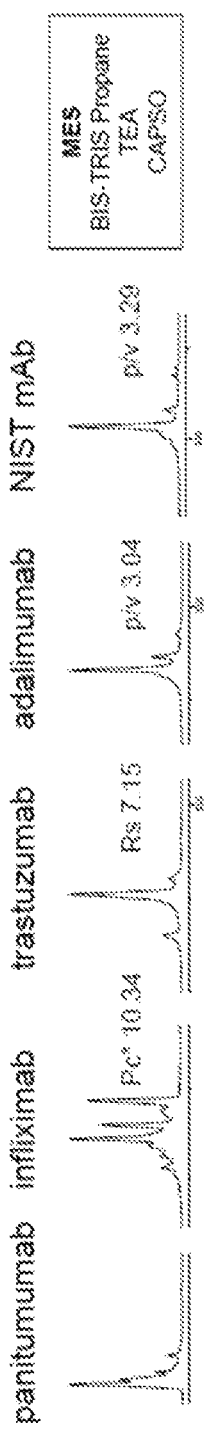
FIGS. 8A-8B show ion exchange chromatograms of panitumumab, infliximab, trastuzumab, adalimumab, and NIST mAb reference material 8671 obtained using buffers composed of MES, BIS-TRIS propane, TEA, and CAPSO (FIG. 8A) or (B) succinic acid, BIS-TRIS propane, TEA, and CAPSO (FIG. 8B).

As seen from the detailed description of certain beneficial embodiments to follow, the present disclosure provides novel mobile phase compositions for facilitating high-resolution, reproducible pH gradient cation exchange separations of mAbs having pI values ranging from 6 to 10, among other uses. These mobile phase compositions allow the use of a binary mobile phase system and were developed by means of empirical optimization according to experimental results linking mobile phase composition to resolving power. In the Examples to follow, the particular mobile phases developed are comprised of four buffer salts, namely a single diprotic acid, a single divalent buffer salt with two amine groups, a single monovalent buffer salt comprising a single amine group, and a single zwitterionic buffer salt. In specific embodiments, the diprotic acid is succinic acid, the divalent buffer salt is BIS-TRIS propane (1,3-bis(tris(hydroxymethyl)methylamino)propane), the monovalent buffer salt is TEA (triethanolamine), and the zwitterionic buffer salt is CAPSO (3-(cyclohexylamino)-2-hydroxy-1-propanesulfonic acid), CAPS (3-(cyclohexylamino)-1-propanesulfonic acid), or β-alanine (3-aminopropanoic acid). In one mobile phase, the buffer salts are titrated to a low pH. In the other mobile phase, the buffer salts are titrated to a high pH and supplemented with a non-buffer salt. The pH range employed is 5.0 to 11.0, and more ideally 5.0 to 10.2, as optimized to achieve balanced resolution of mAbs exhibiting a wide range of pI values. The concentrations of the buffer salts and the non-buffer salt are optimized to achieve high mAb resolution, a linear pH trace, and an advantageous conductivity trace. The developed method delivers high resolution for a wide range of mAbs and good pH linearity with individual buffer salt concentrations ranging from 2 to 20 millimolar, more ideally from 5 to 15 millimolar, and most ideally from 8 to 11 millimolar. To achieve optimal resolving power, the second mobile phase buffer is provided with a non-buffer salt, such as sodium chloride (NaCl) or potassium chloride (KCl), at a concentration of 1 to 100 millimolar, or more ideally 5 to 60 millimolar. This non-buffer salt is added to fine tune the conductivity trace associated with the pH gradient. As well, in a preferred embodiment, the binary gradient change from low to high pH values can also optionally entail a gradient change in the concentration of the buffer salts, including one as large as 30% but also as small as 5%. That is, the first mobile phase contains buffer salt concentrations that are 30%, or more ideally 10%, lower than the second mobile phase.

To evaluate the resolving power of pH gradient ion exchange chromatography, five mAbs (panitumumab, infliximab, trastuzumab, adalimumab, and NIST mAb reference material 8671) were routinely analyzed. An effective peak capacity of infliximab, a pseudo resolution between the acidic variant and the main peak of trastuzumab, and peak-to-valley ratios (p/v) of the first lysine variant of adalimumab and NIST mAb were calculated from UV chromatograms as demonstrated in FIGS. 1A-1D, respectively.

In one exemplary embodiment of present disclosure, the pH gradient buffers are composed of succinic acid, BIS-TRIS propane, TEA, and CAPSO with the composition described in FIG. 2A. When used in combination with a 3 μm non-porous sulfonated cation exchange stationary phase packed into a 4.6×50 mm column dimension, high resolution separations can be achieved for each of the tested mAbs. UV chromatograms corresponding to these analyses are shown in FIG. 2B along with calculated values on peak capacity, resolution, and p/v ratios. Using this method, good resolution could be achieved for each mAb using a rapid 0.23 pH unit/minute gradient.

Buffer salts used in the present Examples are shown the following Table 1:

TABLE 1

| Short Name | IUPAC Name | pKa1 | pKa2 | pKa3 |
|---|---|---|---|---|
| ACES | 2-(carbamoylmethylamino)ethanesulfonic acid | 6.9 | n/a | n/a |
| AMP | 2-amino-2-methyl-1-propanol | 9.7 | n/a | n/a |
| AMPD | 2-amino-2-methyl-1,3-propanediol | 8.8 | n/a | n/a |
| β-alanine | 3-Aminopropanoic acid | 3.6 | 10.4 | n/a |
| BIS-TRIS Propane | 1,3-bis(tris(hydroxymethyl)methylamino)propane | 6.8 | 9.1 | n/a |
| CAPS | 3-(Cyclohexylamino)-1-propanesulfonic acid | 10.4 | n/a | n/a |
| CAPSO | 3-(Cyclohexylamino)-2-hydroxy-1-propanesulfonic acid | 9.6 | n/a | n/a |
| Citric Acid | 2-Hydroxypropane-1,2,3-tricarboxylic acid | 3.1 | 4.8 | 6.4 |
| EPPS | 4-(2-hydroxyethyl)-1-piperazine propanesulfonic acid | 7.9 | n/a | n/a |
| Gly | Aminoethanoic acid | 2.4 | 8.1 | n/a |
| Gly-Gly | 2-[(2-Aminoacetyl)amino]acetic acid | 3.1 | 8.1 | n/a |
| Histidine | 2-Amino-3-(1H-imidazol-4-yl)propanoic acid | 1.8 | 6.1 | 9.2 |
| Imidazole | 1,3-diazacyclopenta-2,4-diene | 7.0 | n/a | n/a |
| MES | 2-morpholin-4-ylethanesulfonic acid | 6.2 | n/a | n/a |
| Piperazine | 1,4-Diazinane | 5.7 | 9.8 | n/a |
| Succinic Acid | 1,4-butandioic acid | 4.1 | 5.5 | n/a |
| TEA | triethanolamine | 7.8 | n/a | n/a |
| Tris | 2-Amino-2-(hydroxymethyl)propane-1,3-diol | 8.1 | n/a | n/a |

Various unexpected results have been observed which have led to the present disclosure. In this regard, the five above-mentioned mAbs were used to evaluate three different comparative pH gradient mobile phase compositions. Chromatograms resulting from the use of buffers based on two zwitterionic buffer salts bearing both carboxyl and amine groups (histidine and Gly-Gly) are shown in FIG. 3A. Noteworthy resolution was observed for panitumumab and the acidic variant of trastuzumab. However, the basic variant of trastuzumab was not well resolved. In addition, only one major peak was observed from infliximab, and resolution for the basic variants of adalimumab and NIST mAb was unsatisfactory. This buffer system was observed to yield a near linear conductivity trace, but its pH trace was seen to be comparatively non-linear, presumably to the detriment of its resolving power. To test another buffer system, trivalent citric acid was combined with glycine and Gly-Gly, and in turn more linear pH and conductivity traces were obtained. High resolution separations were achieved for panitumumab, adalimumab, and NIST mAb, and reasonably good resolution was even seen for the separation of infliximab (FIG. 3A). The basic variant of trastuzumab, however, was not resolved. In yet another buffer composition, a zwitterionic buffer salt bearing both sulfonate and amine groups (MES) was tested in combination with glycine and Gly-Gly. Despite improving the separations of panitumumab, infliximab, and adalimumab and showing reasonably linear pH and conductivity traces, this buffer system did not yield satisfactory separation of the basic variants of trastuzumab and NIST mAb (FIG. 3C). In sum, the above examples demonstrate that mAb separations should be carefully evaluated during the development of pH gradient ion exchange methods and that the utility of various buffer salts cannot be assumed.

Next, alternatives to the preferred buffer composition were explored, and the significance of choosing a divalent buffer salt with two amine groups, specifically, BIS-Tris propane, was substantiated. In contrast to the previous three comparative buffer compositions, a combination of a diprotic acid, specifically, succinic acid, a divalent buffer salt with two amine groups, specifically BIS-TRIS propane, a monovalent buffer salt having an amine group, specifically, TEA, and a zwitterionic buffer salt, specifically, CAPS resulted in notably balanced resolution for infliximab, trastuzumab, adalimumab and NIST mAb (FIG. 4B). Replacing the divalent buffer salt having two amine groups (BIS-TRIS propane), with two buffer salts of comparable pKa values (ACES and AMPD) resulted in similar resolution for panitumumab, infliximab, adalimumab, and the acidic variant of trastuzumab (FIG. 4A). However, resolution on the basic variants of trastuzumab and NIST mAb were better with the buffer containing divalent buffer salt. ACES is a zwitterionic monovalent buffer salt with a sulfonate group and an amine group, and AMPD is a monovalent buffer salt with an amine group. The pH gradient buffer containing a negatively charged sulfonate group from the zwitterionic buffer salt ACES showed lower conductivities at low to medium pH range and have slightly higher conductivities at high pH range compared to the buffer composed of BIS-TRIS propane. Regardless, no benefit to resolution was observed for mAbs with lower to median pI values, and the resolution for higher pI mAbs was better with the buffers composed of BIS-TRIS propane.

In the buffer composed of succinic acid, BIS-TRIS propane, TEA, and CAPS, replacing the zwitterionic CAPS with monovalent AMP resulted in similar resolution for panitumumab, infliximab, trastuzumab, and adalimumab (FIGS. 5A-5B). Although the p/v ratios for the basic variant of NIST mAb were nearly identical using the two buffer compositions, the peak profile obtained with the buffer containing AMP was distorted versus established data sets. The pH traces of the buffers composed of CAPS and AMP were highly similar. However, a concave curve in the conductivity trace was observed at a retention time of 14 minutes when using the buffer composed of AMP, while the conductivity trace remained relatively steady in the same range with the buffer containing CAPS. Without wishing to be bound by theory of operation, the sulfonate group in CAPS is believed to impart a desired linearity to the conductivity trace and, as a consequence, yield reliable peak profiles for mAbs with higher pI values. In this way, buffers comprised of CAPS, but not AMP, are deemed to be beneficial for this method.

When CAPS is replaced by another zwitterionic monovalent buffer salt having a slightly lower pKa value (CAPSO, 9.6 versus 10.4), similar resolution values for panitumumab and infliximab were observed (FIG. 6A-6B). Moreover, the resolution metrics for trastuzumab, adalimumab, and NIST mAb were slightly improved. Since a large portion of mAbs have pI values in the range of 6 to 10, the use of CAPSO may be preferred in some instances. However, in the case of analyzing a mAb with an inordinately high pI, CAPS may be applied to ensure a higher final pH value can be achieved with the described binary gradient. So, while the use of CAPSO is a preferred embodiment in some instances, it could, in other instances, be advantageous to use a buffer containing CAPS.

The replacement of TEA with an alternative buffer salt was also explored. In a buffer composed of succinic acid, BIS-TRIS propane, TEA, and CAPSO, the monovalent buffer salt TEA was replaced with a zwitterionic monovalent buffer salt having a comparable pKa (EPPS) and slightly better resolution was observed for NIST mAb with EPPS. However, the separations of panitumumab, infliximab, trastuzumab, and adalimumab were found to suffer (FIGS. 7A-7B). In addition, a more pronounced baseline shift was observed in the UV chromatograms. Although similar pH traces were observed with the two buffer systems, the conductivity of the buffer system containing EPPS was much higher than the buffer system containing TEA, even though their concentration of non-buffer salt was identical. It appears, as a result, that the buffer system based on TEA gives more balanced capabilities for mAb charge variant profiling. Accordingly, in various beneficial embodiments, TEA is used.

Figure 8B:
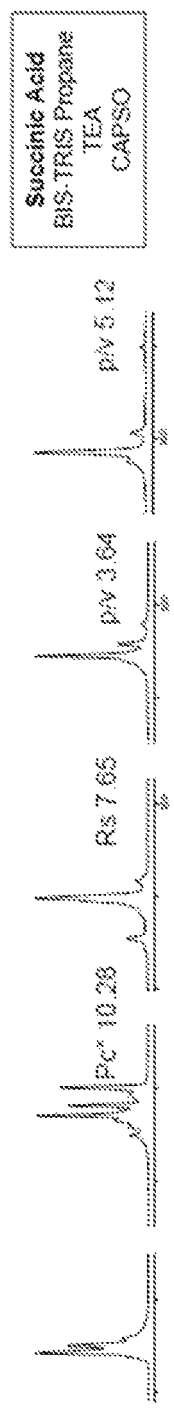
Figure 8C:
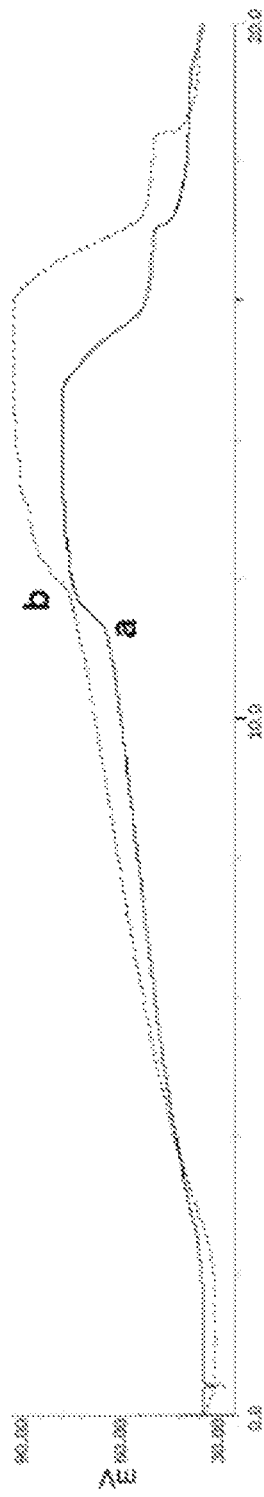
FIG. 8C shows the conductivity traces observed using buffers composed of MES, BIS-TRIS propane, TEA, and CAPSO (solid line), or succinic acid, BIS-TRIS propane, TEA, and CAPSO (dashed line).

In a similar fashion, the changeability of the diprotic acid buffer salt succinic was investigated. In a buffer composed of succinic acid, BIS-Tris propane, TEA, and CAPSO, the diprotic acid buffer salt succinic acid was replaced with a zwitterionic monovalent buffer salt having comparable pKa (MES). However, no benefit to resolution was observed for infliximab, trastuzumab, and adalimumab, despite a reduction in conductivity at medium to high pH ranges (FIGS. 8A-8B). Moreover, the low pI mAb, panitumumab, was poorly retained with the alternative MES buffer. Furthermore, resolution for NIST mAb was noticeably worse. Thus, a buffer containing the diprotic acid buffer salt succinic acid, rather than the zwitterionic monovalent buffer salt MES, is preferred.

Figure 9A:
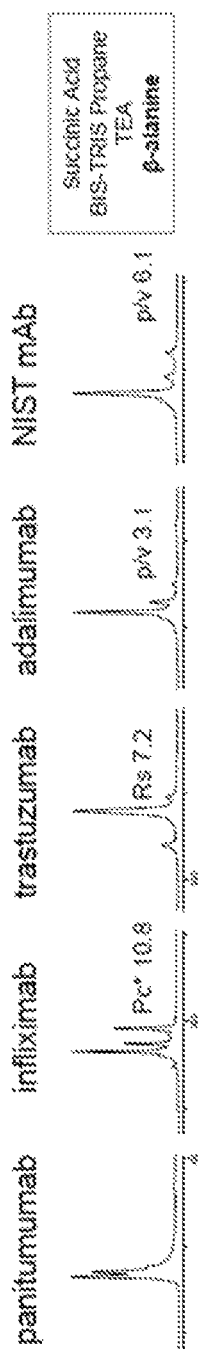
FIGS. 9A-9B show ion exchange chromatograms of panitumumab, infliximab, trastuzumab, adalimumab, and NIST mAb reference material 8671 obtained using buffers composed of succinic acid, BIS-TRIS propane, TEA, and β-alanine (FIG. 9A) or (B) succinic acid, BIS-TRIS propane, TEA, and CAPS (FIG. 9B).
Figure 9B:
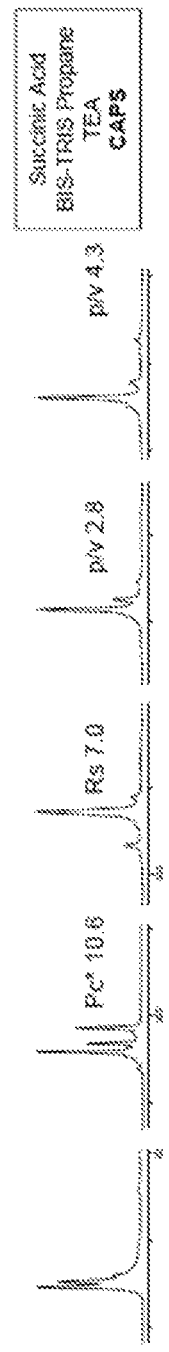
Figure 10A:
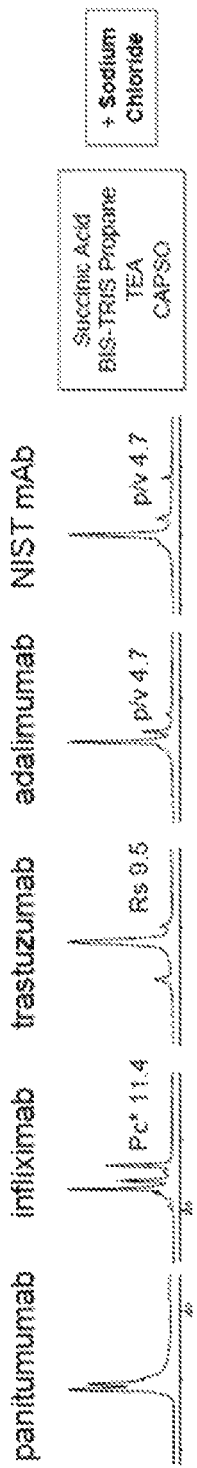
FIGS. 10A-10B show ion exchange chromatograms of panitumumab, infliximab, trastuzumab, adalimumab, and NIST mAb reference material 8671 obtained using buffers composed of succinic acid, BIS-TRIS propane, TEA, and CAPSO and the ionic strengths were mediated with sodium chloride (FIG. 10A) or potassium chloride (FIG. 10B).
Figure 10B:
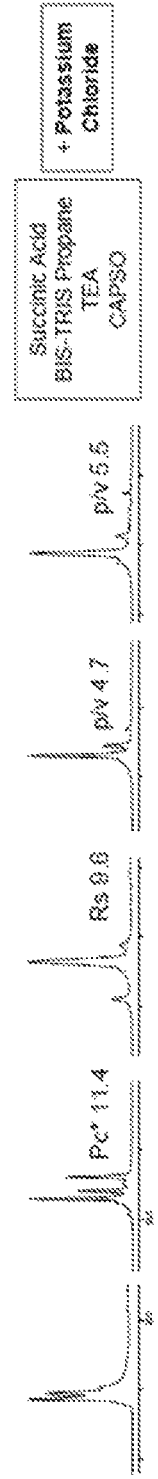

Given the above results, it has been determined that a buffer system based on succinic acid, BIS-Tris propane, TEA, and CAPSO affords a highly capable mAb charge profiling method (FIG. 2B). Nevertheless, it should be recognized that several alternative buffer systems could also be effectively used. For example, CAPSO can be successfully replaced with either CAPS or β-alanine. In both cases, reasonably high resolution can be achieved for panitumumab, infliximab, trastuzumab, adalimumab and NIST mAb (FIGS. 9A-9B). In addition, with either buffer system, the pH and conductivity traces were found to be relatively linear. In this way, other zwitterionic buffer salts with a carboxyl group, such as amino acids or short peptides are expected to be suitable for use in combination with succinic acid, BIS-Tris propane, and TEA. In another alternative embodiment, the non-buffer salt sodium chloride can be replaced with potassium chloride without compromising resolution capabilities (FIGS. 10A-10B). In certain beneficial embodiments, the concentration of the non-buffer salt in the second mobile phase buffer is 1 to 100 millimolar, and more ideally 5 to 60 millimolar.

Based on exploration of pH gradient buffer compositions, the pH range of buffers composed of succinic acid, BIS-Tris propane, TEA, and CAPSO was optimized by varying the pH of the first mobile phase buffer (buffer A) from 3.5 to 5.5 while keeping the pH of the second mobile phase buffer (buffer B) at 10.2. The peak capacities of infliximab and the p/v ratios of the basic variant of NIST mAb were found to improve slightly as the pH of buffer A increased from 3.5 to 5.5. Meanwhile, the resolution of trastuzumab and adalimumab remained relatively constant (FIGS. 11A-11E). Most notably, the retention of panitumumab, a mAb with a pI of 6.7, was poor when the pH of buffer A was titrated to 5.5 (FIG. 11E). Lowering the pH of buffer A to 5.2 improved the retention of panitumumab, but the peak profile was somewhat distorted comparing to established results (FIG. 11D). Hence, in a certain beneficial embodiments, a buffer system composed of succinic acid, BIS-TRIS propane, TEA, and CAPSO is prepared so as to have one mobile phase titrated to a pH of 5.0 and the other to 10.2.

Figures 13A, 13B, 13C, 13D:
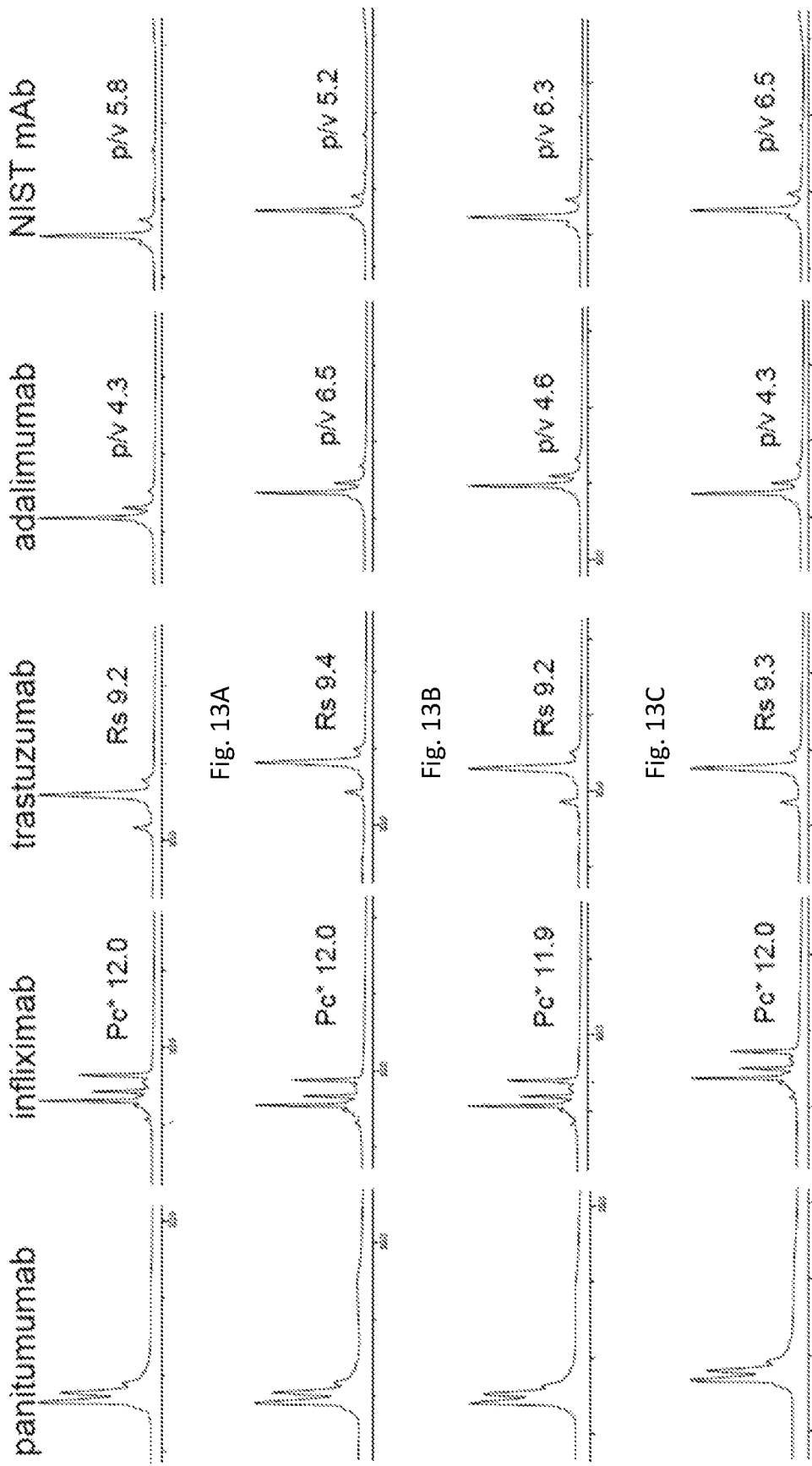
FIGS. 13A-13H show ion exchange chromatograms of panitumumab, trastuzumab, adalimumab, and NIST mAb reference material 8671 obtained using buffers composed of succinic acid, BIS-TRIS propane, TEA, and CAPSO with the ionic strengths of buffer salts as specified in FIG. 12A. In particular.
Figures 13E, 13F, 13G, 13H:
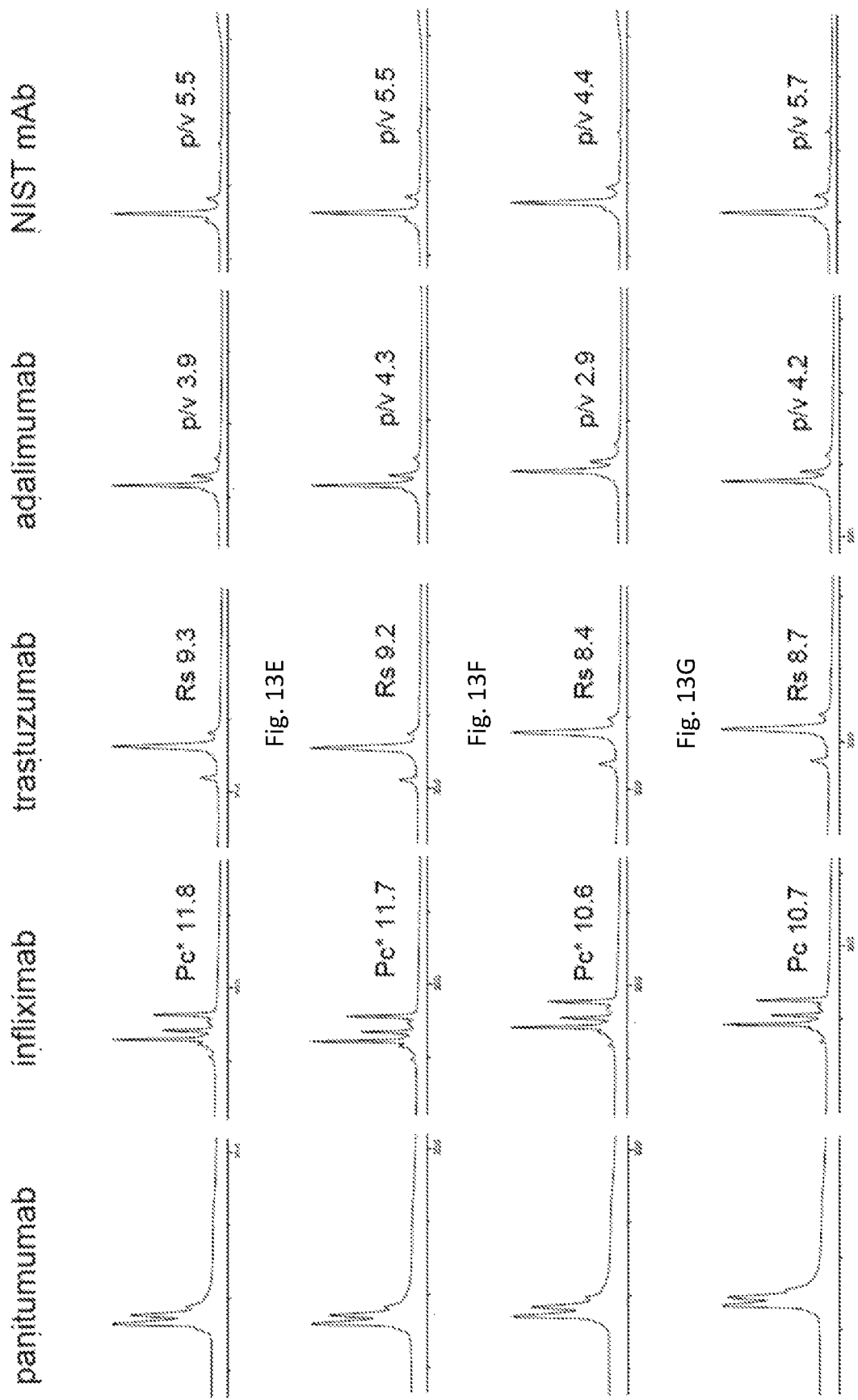

In another study, the concentrations of the components in the preferred buffer system were optimized. Buffer composition a in FIG. 12A was taken as a starting point to optimize for linear pH traces across a gradient between pH 5.0 and 10.2. Although this buffer composition is effective in providing a linear pH trace at relatively shallow gradients, it was found that an experimental pH trace obtained with a rapid gradient of 0.46 pH unit/minute showed deviations from a theoretical, linear trace (FIG. 12B). In an attempt to mitigate kinetic effects, the present inventors also empirically evaluated how the linearity of the pH trace was affected by changes to the concentrations of each individual buffer salts. Through this work, it was seen that increasing the concentrations of BIS-Tris propane or CAPSO gave slight improvements to pH linearity. Conversely, changing the concentrations of TEA did not appear to have a significant effect (FIG. 12B-12G). In turn, the present inventors were successful in determining an optimal ratio of succinic acid:BIS-TRIS propane:TEA:CAPSO (FIG. 12H). By evaluating effects on mAb resolution, an effective concentration range for each individual buffer salt was determined. Chromatograms obtained with various buffers (a-h) are shown in FIGS. 13A-13H. Varying the concentration of BIS-Tris propane by ±25% from 8.3 mM did not affect the resolution of infliximab or trastuzumab, but it did appear to cause slight fluctuations in the resolution of the basic variants of adalimumab and NIST mAb (FIGS. 13A-13C). Similarly, varying the concentration of CAPSO by ±33% from 6.0 mM and the concentration of TEA by ±22% from 9.0 mM only resulted in slight fluctuations of the resolution for the five tested mAbs (FIGS. 13D-13G). Ultimately, the separations observed for infliximab, trastuzumab, adalimumab and NIST mAb with buffer h were comparable to the results achieved with buffers a-g (FIG. 13H). However, it was noticed that the resolution of panitumumab with buffer h was compromised if compared to buffers a-g, likely due to its relatively high ionic strength. In order to improve the resolution of a low pI mAb, the concentrations of the four buffer salts in mobile phase A were each decreased by 10% (FIGS. 14A-14B). In doing this, the resolution of panitumumab visibly improved, while the resolution of the other mAbs remained unchanged (FIG. 14B). In a preferred embodiment, the pH gradient buffer system of this disclosure is comprised of individual buffer salts (for example succinic acid, BIS-TRIS propane, TEA, and CAPSO) at concentrations ranging from 2 to 20 mM. As well, in a preferred embodiment, the binary gradient corresponding to the lowest and highest pH values can also optionally include a gradient change in the concentration of the buffer salts, including a gradient change as large as 30% but also as small as 5%.

The chromatographic capabilities of the developed pH gradient buffer system are exemplary and this can be visualized in a comparative example. To this end, a study was performed to compare the buffer system of this disclosure to that prepared by a commercially-available product from Thermo Scientific (CX-1 Buffer Kit) (Fekete, S.; Beck, A.; Fekete, J.; Guillarme, D., "Method development for the separation of monoclonal antibody charge variants in cation exchange chromatography, Part II: pH gradient approach." *Journal of pharmaceutical and biomedical analysis* 2015, 102, 282-9) and a previously published buffer system (see Zhang et al., supra). Direct comparisons of mAb charge variant separations using these three salt-mediated pH gradient cation exchange chromatography methods were performed using a 3 μm non-porous sulfonated cation exchange stationary phase and gradients of matching slope (0.23 pH unit/minute). Implementation of the buffer system described by Zhang et al. (composed of piperazine, imidazole, and Tris) failed to provide robust separations of medium to high pI mAbs, although the low pI mAb, panitumumab, was well resolved (FIG. 15A). The inadequacy of this method in the present case originates from the fact that it was designed for use with a carboxymethyl weak cation exchange stationary phase and not a sulfonated strong cation exchange stationary phase. In contrast, the CX-1 buffer kit was designed to be used with either type of ion exchanger. Versus the buffer system described herein, similar resolution for infliximab and trastuzumab could be achieved with the mobile phases prepared with a Thermo CX-1 Buffer Kit (FIGS. 15B and 15C). However, through this comparison, enhanced resolution for high pI mAbs, e.g. adalimumab and NIST mAb, was achieved with the compositions of the present disclosure. In summary, the buffer system of this disclosure has been found to provide the most balanced resolving power for mAb charge variant profiling. Additionally, it has been found that it is particularly advantageous to employ the inventive compositions with a 3 μm non-porous sulfonated strong cation exchange stationary phase. That is, the mobile phase buffer system describe here in would be ideal in pairing with the cation exchange stationary phases described in U.S. Provisional Patent Application No. 62/635,699, filed Feb. 27, 2018 and entitled "Polymer Particles with a Gradient Composition and Methods of Production Thereof" which is hereby incorporated by reference. Additionally, this mobile phase buffer system could be advantageously paired with other cation exchange columns, including but not limited to Thermo Scientific MAb Pac SCX, Thermo Scientific Pro Pac SCX, Thermo Scientific Pro Pac WCX, and YMC BioPro SP-F.

As seen from the above, advantages of the present disclosure include the ability to perform charge variant profiling of mAb-based therapeutics with enhanced peak resolution and reproducibility.

Although optimized to achieve high resolution for mAb charge variants, the methods, compositions and kits described herein can be used to separate other analytes, including other types of biomolecules, particular examples of which include peptides, other proteins including naturally occurring non-mAb proteins, fusion proteins and antibody drug conjugates (ADCs), among others.

Further aspects of the present disclosure will now be described in the following enumerated paragraphs.

Aspect A1. A chromatographic elution buffer solution comprising (a) a first buffer salt comprising a first pKa value, (b) a second buffer salt comprising a second pKa value, (c) a third buffer salt comprising a third pKa value, and (d) a fourth buffer salt comprising a fourth pKa value, wherein the first pKa value is less than the second pKa value, wherein the second pKa value is less than the third pKa value, and wherein the third pKa value is less than the fourth pKa value, and wherein the buffer solution has a pH ranging from 3 to 11.

Aspect A2. The chromatographic elution buffer of Aspect A1, wherein the first pKa value differs from the second pKa value by a first amount ranging from 0.2-2.0, wherein the second pKa value differs from the third pKa value by a second amount ranging from 0.2-2.0, and wherein the third pKa value differs from the fourth pKa value by a third amount ranging from 0.2-2.0.

Aspect A3. The chromatographic elution buffer of Aspect A1, wherein the first pKa value ranges from 3 to 5, wherein the second pKa value ranges from 5 to 7, wherein the third pKa value ranges from 7 to 9, and wherein the fourth pKa value ranges from 9 to 11.

Aspect A4. A chromatographic elution buffer solution of any of Aspects A1-A3, wherein the first buffer salt is a diprotic acid, (b) wherein the second buffer salt is a divalent buffer salt with two amine groups, (c) wherein the third buffer salt is a monovalent buffer salt comprising a single amine group, and (d) wherein the fourth buffer salt is a zwitterionic buffer salt.

Aspect A5. The chromatographic elution buffer of Aspect A4, wherein the diprotic acid buffer salt is succinic acid.

Aspect A6. The chromatographic elution buffer of any of Aspects A4-A5, wherein the divalent buffer salt is BIS-TRIS propane.

Aspect A7. The chromatographic elution buffer of any of Aspects A4-A6, wherein the monovalent buffer salt is selected from triethanolamine and TRIS.

Aspect A8. The chromatographic elution buffer of any of Aspects A4-A7, wherein the zwitterionic buffer salt is selected from zwitterionic buffer salt comprising a sulfonate group and an amine group and a zwitterionic buffer salt comprising a carboxyl group and an amine group.

Aspect A9. The chromatographic elution buffer of any of Aspects A4-A8, wherein the zwitterionic buffer salt is selected from CAPSO, CAPS and β-alanine.

Aspect A10. A chromatographic elution buffer kit comprising (a) a first buffer solution comprising a chromatographic elution buffer in accordance with any of Aspects A1-9, wherein the buffer solution has a pH ranging from 3 to 7 or has a pH ranging from 3 to 7 upon dilution with water in a ratio ranging from 1:2 to 1:20 and (b) a second buffer solution comprising a chromatographic elution buffer in accordance with any of Aspects A1-9 and further comprising a non-buffer salt, wherein the second buffer solution has a pH ranging from 9 to 11 or has a pH ranging from 9 to 11 upon dilution with water in a ratio ranging from 1:2 to 1:20.

Aspect A11. The chromatographic elution buffer kit of Aspect A10, wherein each of the first, second, third and fourth buffer salts is present in the first buffer solution at a concentration ranging from 2 to 20 millimolar and/or wherein each of the first, second, third and fourth buffer salts is present in the second buffer solution at a concentration ranging from 2 to 20 millimolar.

Aspect A12. The chromatographic elution buffer kit of any of Aspects A10-A11, wherein the non-buffer salt comprises (a) a cation selected from alkali metal cations, alkaline earth metal cations, transition metal cations, ammonium cations and (b) an anion selected from selected from halide anions, nitrate anions, sulfate anions, phosphate anions, carbonate anions, chlorate anions, thiocyanate anions and perchlorate anions Aspect A13. The chromatographic elution buffer kit of Aspect A12, wherein the concentration of the non-buffer salt ranges from 1 to 100 millimolar.

Aspect A14. The chromatographic elution buffer kit of any of Aspects A10-A13, wherein a concentration of each of the first, second, third and fourth buffer salts in the first buffer solution is from 10% to 30% lower than a concentration of each of the first, second, third and fourth buffer salts in the second buffer solution.

Aspect A15. The chromatographic elution buffer kit of any of Aspects A10-A13, wherein a total concentration of the first, second, third and fourth buffer salts in the first buffer solution is from 10% to 30% lower than a total concentration of the first, second, third and fourth buffer salts in the second buffer solution.

Aspect A16. The chromatographic elution buffer kit of any of Aspects A10-A14, wherein a plot of pH versus volume percent of the first buffer solution relative to a total volume for a binary mixture of the first buffer solution and the second buffer solution is linear.

Aspect A17. The chromatographic elution buffer kit of any of Aspects A10-A16, wherein a plot of conductivity versus volume percent of the first buffer solution relative to a total volume for a binary mixture of the first buffer solution and the second buffer solution is linear.

Aspect A18. The chromatographic elution buffer kit of any of Aspects A10-A14, wherein a plot of conductivity versus volume percent of the first buffer solution relative to a total volume for a binary mixture of the first buffer solution and the second buffer solution does not exhibit a negative slope.

Aspect A19. The chromatographic elution buffer kit of any of Aspects A10-A17, wherein the first buffer solution has a conductivity ranging from 0.5 millisiemins (mS) to 3 mS and wherein the second buffer solution has a conductivity ranging from 3 mS to 100 mS.

Aspect A20. The chromatographic elution buffer kit of any of Aspects A10-A19, further comprising an ion-exchange chromatography material.

Aspect A21. The chromatographic elution buffer kit of Aspect A20, comprising a separation device comprising a housing comprising an inlet and an outlet that is configured to accept and hold the ion-exchange chromatography material.

Aspect A22. The chromatographic elution buffer kit of any of Aspects A20-A21, wherein the ion-exchange chromatography material is a cation exchange chromatography material.

Aspect A23. The chromatographic elution buffer kit of Aspect A22, wherein the cation exchange chromatography material comprises carboxylate groups.

Aspect A24. The chromatographic elution buffer kit of Aspect A22, wherein the cation exchange chromatography material comprises sulfonate groups.

Aspect A25. A method for analyzing a sample comprising a plurality of analytes, the method comprising: loading the sample onto an ion-exchange chromatography material thereby binding the plurality of analytes to the ion-exchange chromatography material and eluting the plurality of analytes from the ion-exchange chromatography material with a mobile phase comprising a chromatographic elution buffer in accordance with any of Aspects A1-9, thereby separating at least some of the plurality of analytes.

Aspect A26. The method of Aspect A25, wherein eluting the plurality of analytes from the ion-exchange chromatography material with the mobile phase comprises a course of elution in which a pH of the mobile phase is altered over time, in which an ionic strength of the mobile phase is altered over time, or both.

Aspect A27. The method of Aspect A25, wherein eluting the plurality of analytes from the ion-exchange chromatography material with the mobile phase comprises a course of elution in which a pH of the mobile phase is increased over time, in which an ionic strength of the mobile phase is increased over time, or both.

Aspect A28. The method of any of Aspects A26-A27, wherein the pH of the mobile phase is increased during the course of elution.

Aspect A29. The method of Aspect A28, wherein the pH of the mobile phase increases from 5.0 to 11.0 during the course of elution.

Aspect A30. The method of any of Aspects A28-A29, wherein there is a linear increase in the pH of the mobile phase during the course of elution.

Aspect A31. The method of any of Aspects A26-A30, wherein the ionic strength of the mobile phase is increased during the course of elution.

Aspect A32. The method of any of Aspects A26-A30, wherein there is a linear increase in the ionic strength of the mobile phase during the course of elution.

Aspect A33. The method of any of Aspects A26-A32, wherein a conductivity of the mobile phase increases during the course of elution.

Aspect A34. The method of any of Aspects A26-A32, wherein there is a linear increase in the conductivity during the course of elution.

Aspect A35. The method of any of Aspects A33-A34, wherein the conductivity of the mobile phase increases between 1.5-fold and 10-fold during the course of elution.

Aspect A36. The method of any of Aspects A33-A35, wherein the conductivity of the mobile phase increases from a first value between 0.5 mS and 3 mS to a second value between 3 mS and 100 mS during the course of elution.

Aspect A37. The method of any of Aspects A26-A36, wherein a concentration of each of the first, second, third and fourth buffer salts in the mobile phase increases between 10% and 40% during the course of elution.

Aspect A38. The method of any of Aspects A26-A36, wherein a total concentration of all of the first, second, third and fourth buffer salts in the mobile phase increases between 10% to 45% during the course of elution.

Aspect A39. The method of any of Aspects A26-A38, wherein an automated system is used to mix two or more solutions to form the mobile phase.

Aspect A40. The method of any of Aspects A26-A38, wherein an automated system is used to mix three or more solutions to form the mobile phase.

Aspect A41. The method of any of Aspects A26-A40, wherein during at least a portion of the course of elution, the mobile phase comprises a non-buffer salt.

Aspect A42. The method of Aspect A41, wherein the course of elution comprises a period during which a concentration of the non-buffer salt increases over time.

Aspect A43. The method of any of Aspects A41-A42, wherein during the course of elution the mobile phase is formed from a buffer mixture that comprises (a) a first buffer solution comprising the first, second, third and fourth buffer salts, the first buffer solution having a pH ranging from 3 to 7 and (b) a second buffer solution comprising the first, second, third and fourth buffer salts and further comprising the non-buffer salt, the second buffer solution having a pH ranging from 9 to 11.

Aspect A44. The method of Aspect A35, wherein the buffer mixture comprises a binary mixture of the first buffer solution and the second buffer solution.

Aspect A45. The method of any of Aspects A43-A44, wherein during the course of elution a first volume percent of the first buffer solution in the buffer mixture is decreased over time while at the same time increasing a second volume percent of the second buffer solution over time in a concentration gradient separation Aspect A46. The method of Aspect A45, wherein the first volume percent in the buffer mixture decreases linearly over time and the second volume percent in the buffer mixture increases linearly during the course of elution.

Aspect A47. The method of any of Aspects A25-A46, further comprising detecting the plurality of analytes.

Aspect A48. The method of any of Aspects A25-A47, wherein the plurality of analytes comprises a plurality of biomolecules.

Aspect A49. The method of any of Aspects A25-A47, wherein the plurality of analytes comprises a plurality of proteins.

Aspect A50. The method of any of Aspects A25-A47, wherein the plurality of analytes comprises a plurality of mAb species having pI values ranging from 6 to 10.

Aspect B1. A chromatographic elution buffer solution comprising a plurality of buffer salts, the buffer solution having a first pKa value that ranges from 4.5 to 6.5, a second pKa value that ranges from 6.5 to 7.5, a third pKa value that ranges from 7.5 to 8.5, a fourth pKa value that ranges from 8.5 to 9.5, and a fifth pKa value that ranges from 9.5 to 11.

Aspect B2. The chromatographic elution buffer solution of Aspect B1, wherein the buffer solution has a pH ranging from 3 to 11.

Aspect B3. The chromatographic elution buffer solution of any of Aspects B1-B2, wherein the first pKa value is provided by a first buffer salt that is a diprotic acid, (b) wherein the second pKa value and the fourth pKa value are provided by a second buffer salt that is a divalent buffer salt with two amine groups, (c) wherein the third pKa is provided by a third buffer salt that is a monovalent buffer salt comprising a single amine group, and (d) wherein the fifth pKa value is provided by a forth buffer salt that is a zwitterionic buffer salt.

Aspect B4. The chromatographic elution buffer solution of Aspect B3, comprising a single zwitterionic buffer salt.

Aspect B5. The chromatographic elution buffer of any of Aspects B3-B4, wherein the diprotic acid buffer salt is succinic acid.

Aspect B6. The chromatographic elution buffer of any of Aspects B3-B5, wherein the divalent buffer salt is BIS-TRIS propane.

Aspect B7. The chromatographic elution buffer of any of Aspects B3-B6, wherein the monovalent buffer salt is selected from triethanolamine and TRIS.

Aspect B8. The chromatographic elution buffer of any of Aspects B3-B7, wherein the zwitterionic buffer salt is selected from zwitterionic buffer salt comprising a sulfonate group and an amine group and a zwitterionic buffer salt comprising a carboxyl group and an amine group.

Aspect B9. The chromatographic elution buffer of any of Aspects B3-B8, wherein the zwitterionic buffer salt is selected from CAPSO, CAPS and βalanine.

Aspect B10. A chromatographic elution buffer kit comprising (a) a first buffer solution comprising a chromatographic elution buffer in accordance with any of Aspects B1-B9, wherein the buffer solution has a pH ranging from 3 to 7 or has a pH ranging from 3 to 7 upon dilution with water in a ratio ranging from 1:2 to 1:20 and (b) a second buffer solution comprising a chromatographic elution buffer in accordance with any of Aspects B1-B9 and further comprising a non-buffer salt, wherein the second buffer solution has a pH ranging from 9 to 11 or has a pH ranging from 9 to 11 upon dilution with water in a ratio ranging from 1:2 to 1:20.

Aspect B11. The chromatographic elution buffer kit of Aspect B10, wherein each of the first, second, third and fourth buffer salts is present in the first buffer solution at a concentration ranging from 2 to 20 millimolar and/or wherein each of the first, second, third and fourth buffer salts is present in the second buffer solution at a concentration ranging from 2 to 20 millimolar.

Aspect B12. The chromatographic elution buffer kit of any of Aspects B10-B11, wherein the non-buffer salt comprises (a) a cation selected from alkali metal cations, alkaline earth metal cations, transition metal cations, ammonium cations and (b) an anion selected from selected from halide anions, nitrate anions, sulfate anions, phosphate anions, carbonate anions, chlorate anions, thiocyanate anions and perchlorate anions Aspect B13. The chromatographic elution buffer kit of Aspect B12, wherein the concentration of the non-buffer salt ranges from 1 to 100 millimolar.

Aspect B14. The chromatographic elution buffer kit of any of Aspects B10-B13, wherein a concentration of each of the first, second, third and fourth buffer salts in the first buffer solution is from 10% to 30% lower than a concentration of each of the first, second, third and fourth buffer salts in the second buffer solution.

Aspect B15. The chromatographic elution buffer kit of any of Aspects B10-B13, wherein a total concentration of the first, second, third and fourth buffer salts in the first buffer solution is from 10% to 30% lower than a total concentration of the first, second, third and fourth buffer salts in the second buffer solution.

Aspect B16. The chromatographic elution buffer kit of any of Aspects B10-B14, wherein a plot of pH versus volume percent of the first buffer solution relative to a total volume for a binary mixture of the first buffer solution and the second buffer solution is linear.

Aspect B17. The chromatographic elution buffer kit of any of Aspects B10-B16, wherein a plot of conductivity versus volume percent of the first buffer solution relative to a total volume for a binary mixture of the first buffer solution and the second buffer solution is linear.

Aspect B18. The chromatographic elution buffer kit of any of Aspects B10-B14, wherein a plot of conductivity versus volume percent of the first buffer solution relative to a total volume for a binary mixture of the first buffer solution and the second buffer solution does not exhibit a negative slope.

Aspect B19. The chromatographic elution buffer kit of any of Aspects B10-B17, wherein the first buffer solution has a conductivity ranging from 0.5 millisiemins (mS) to 3 mS and wherein the second buffer solution has a conductivity ranging from 3 mS to 100 mS.

Aspect B20. The chromatographic elution buffer kit of any of Aspects B10-B19, further comprising an ion-exchange chromatography material.

Aspect B21. The chromatographic elution buffer kit of Aspect B20, comprising a separation device comprising a housing comprising an inlet and an outlet that is configured to accept and hold the ion-exchange chromatography material.

Aspect B22. The chromatographic elution buffer kit of any of Aspects B20-B21, wherein the ion-exchange chromatography material is a cation exchange chromatography material.

Aspect B23. The chromatographic elution buffer kit of Aspect B22, wherein the cation exchange chromatography material comprises carboxylate groups.

Aspect B24. The chromatographic elution buffer kit of Aspect B22, wherein the cation exchange chromatography material comprises sulfonate groups.

Aspect B25. A method for analyzing a sample comprising a plurality of analytes, the method comprising: loading the sample onto an ion-exchange chromatography material thereby binding the plurality of analytes to the ion-exchange chromatography material and eluting the plurality of analytes from the ion-exchange chromatography material with a mobile phase comprising a chromatographic elution buffer in accordance with any of Aspects B1-9, thereby separating at least some of the plurality of analytes.

Aspect B26. The method of Aspect B25, wherein eluting the plurality of analytes from the ion-exchange chromatography material with the mobile phase comprises a course of elution in which a pH of the mobile phase is altered over time, in which an ionic strength of the mobile phase is altered over time, or both.

Aspect B27. The method of Aspect B25, wherein eluting the plurality of analytes from the ion-exchange chromatography material with the mobile phase comprises a course of elution in which a pH of the mobile phase is increased over time, in which an ionic strength of the mobile phase is increased over time, or both.

Aspect B28. The method of any of Aspects B26-B27, wherein the pH of the mobile phase is increased during the course of elution.

Aspect B29. The method of Aspect B28, wherein the pH of the mobile phase increases from 5.0 to 11.0 during the course of elution.

Aspect B30. The method of any of Aspects B28-B29, wherein there is a linear increase in the pH of the mobile phase during the course of elution.

Aspect B31. The method of any of Aspects B26-B30, wherein the ionic strength of the mobile phase is increased during the course of elution.

Aspect B32. The method of any of Aspects B26-B30, wherein there is a linear increase in the ionic strength of the mobile phase during the course of elution.

Aspect B33. The method of any of Aspects B26-B32, wherein a conductivity of the mobile phase increases during the course of elution.

Aspect B34. The method of any of Aspects B26-B32, wherein there is a linear increase in the conductivity during the course of elution.

Aspect B35. The method of any of Aspects B33-B34, wherein the conductivity of the mobile phase increases between 1.5-fold and 10-fold during the course of elution.

Aspect B36. The method of any of Aspects B33-B35, wherein the conductivity of the mobile phase increases from a first value between 0.5 mS and 3 mS to a second value between 3 mS and 100 mS during the course of elution.

Aspect B37. The method of any of Aspects B26-B36, wherein a concentration of each of the first, second, third and fourth buffer salts in the mobile phase increases between 10% and 40% during the course of elution.

Aspect B38. The method of any of Aspects B26-B36, wherein a total concentration of all of the first, second, third and fourth buffer salts in the mobile phase increases between 10% to 45% during the course of elution.

Aspect B39. The method of any of Aspects B26-B38, wherein an automated system is used to mix two or more solutions to form the mobile phase.

Aspect B40. The method of any of Aspects B26-B38, wherein an automated system is used to mix three or more solutions to form the mobile phase.

Aspect B41. The method of any of Aspects B26-B40, wherein during at least a portion of the course of elution, the mobile phase comprises a non-buffer salt.

Aspect B42. The method of Aspect B41, wherein the course of elution comprises a period during which a concentration of the non-buffer salt increases over time.

Aspect B43. The method of any of Aspects B41-B42, wherein during the course of elution the mobile phase is formed from a buffer mixture that comprises (a) a first buffer solution comprising the first, second, third and fourth buffer salts, the first buffer solution having a pH ranging from 3 to 7 and (b) a second buffer solution comprising the first, second, third and fourth buffer salts and further comprising the non-buffer salt, the second buffer solution having a pH ranging from 9 to 11.

Aspect B44. The method of Aspect B35, wherein the buffer mixture comprises a binary mixture of the first buffer solution and the second buffer solution.

Aspect B45. The method of any of Aspects B43-B44, wherein during the course of elution a first volume percent of the first buffer solution in the buffer mixture is decreased over time while at the same time increasing a second volume percent of the second buffer solution over time in a concentration gradient separation Aspect B46. The method of Aspect B45, wherein the first volume percent in the buffer mixture decreases linearly over time and the second volume percent in the buffer mixture increases linearly during the course of elution.

Aspect B47. The method of any of Aspects B25-B46, further comprising detecting the plurality of analytes.

Aspect B48. The method of any of Aspects B25-B47, wherein the plurality of analytes comprises a plurality of biomolecules.

Aspect B49. The method of any of Aspects B25-B47, wherein the plurality of analytes comprises a plurality of proteins.

Aspect B50. The method of any of Aspects B25-B47, wherein the plurality of analytes comprises a plurality of mAb species having pI values ranging from 6 to 10.

Further aspects of the present disclosure are detailed in the Examples to follow.

Example 1. Ion Exchange Chromatography with Buffers Composed of Succinic Acid, BIS-TRIS Propane, TEA, and CAPSO FIGS. 2 and 15C present chromatograms obtained with the buffer compositions, LC conditions, and gradient table listed below:

TABLE 2

Buffer Compositions:

| mM | Succinic acid | Bis-Tris Propane | TEA | CAPSO | NaCl | pH |
|---|---|---|---|---|---|---|
| Buffer A | 9.5 | 9.9 | 8.1 | 9.9 | 0 | 5.03 |
| Buffer B | 10.5 | 11.0 | 9.0 | 11.0 | 40.0 | 10.27 |

TABLE 3

LC Conditions

| | |
|---|---|
| System | ACQUITY UPLC H-Class Bio |
| Column Stationary Phase: | 3 μm non-porous sulfonated strong cation exchange stationary phase |
| Column Dimension | 4.6 × 50 mm |
| Sample: | Dilute panitumumab, infliximab, trastuzumab, adalimumab, and NIST mAb with 18.2 MΩ purified water to concentrations of 5 mg/ml |
| Flow Rate: | 0.72 mL/min |
| Column Temperature: | 30° C. |
| Injection Volume: | 5 μL |
| Detection: | 280 nm |

TABLE 4

Gradient Table:

| Time(min) | Flow Rate(mL/min) | % A | % B | Curve |
|---|---|---|---|---|
| Initial | 0.720 | 100 | 0 | Initial |
| 1.00 | 0.720 | 100 | 0 | 6 |

TABLE 4-continued

Gradient Table:

| Time(min) | Flow Rate(mL/min) | % A | % B | Curve |
|---|---|---|---|---|
| 23.60 | 0.720 | 0 | 100 | 6 |
| 26.60 | 0.720 | 0 | 100 | 6 |
| 27.60 | 0.720 | 100 | 0 | 6 |
| 40.00 | 0.720 | 100 | 0 | 6 |

FIG. 8B present chromatograms obtained with the buffer compositions and LC conditions listed above, and gradient table listed below:

TABLE 5

Gradient Table:

| Time(min) | Flow Rate(mL/min) | % A | % B | Curve |
|---|---|---|---|---|
| Initial | 0.720 | 100 | 0 | Initial |
| 1.00 | 0.720 | 100 | 0 | 6 |
| 12.30 | 0.720 | 0 | 100 | 6 |
| 15.30 | 0.720 | 0 | 100 | 6 |
| 16.30 | 0.720 | 100 | 0 | 6 |
| 20.00 | 0.720 | 100 | 0 | 6 |

FIGS. 6B, 7B, 10A, and 11A present chromatograms obtained with the buffer compositions, LC conditions, and gradient table listed below, and FIG. 10B presents chromatograms obtained with the buffer compositions, LC conditions, and gradient table listed below except sodium chloride in buffer C was replaced with potassium chloride:

TABLE 6

Buffer Compositions:

| mM | succinic acid | Bis-Tris Propane | TEA | CAPSO | NaCl | pH |
|---|---|---|---|---|---|---|
| Buffer A | 7.5 | 7.5 | 7.5 | 10.5 | 0 | 3.50 |
| Buffer B | 7.5 | 9.0 | 7.5 | 7.5 | 0 | 10.20 |
| Buffer C | 0 | 0 | 0 | 0 | 500 | not adjusted |

TABLE 7

LC Conditions

| | |
|---|---|
| System | ACQUITY UPLC H-Class Bio |
| Column Stationary Phase: | 3 μm non-porous sulfonated strong cation exchange stationary phase |
| Column Dimension | 2.1 × 50 mm |
| Sample: | Dilute panitumumab, infliximab, trastuzumab, adalimumab, and NIST mAb with 18.2 MΩ purified water to concentrations of 5 mg/mL |
| Flow Rate: | 0.15 mL/min |
| Column Temperature: | 30° C. |
| Injection Volume: | 1 μL |
| Detection: | 280 nm |

TABLE 8

Gradient Table:

| Time(min) | Flow Rate(mL/min) | % A | % B | % C | Curve |
|---|---|---|---|---|---|
| Initial | 0.150 | 100 | 0 | 0 | Initial |
| 1.00 | 0.150 | 100 | 0 | 0 | 6 |
| 15.60 | 0.150 | 0 | 92 | 8 | 6 |

TABLE 8-continued

Gradient Table:

| Time(min) | Flow Rate(mL/min) | % A | % B | % C | Curve |
|---|---|---|---|---|---|
| 18.60 | 0.150 | 0 | 92 | 8 | 6 |
| 19.60 | 0.150 | 100 | 0 | 0 | 6 |
| 25.00 | 0.150 | 100 | 0 | 0 | 6 |

FIG. 11B presents chromatograms obtained with the buffer compositions listed for FIG. 11A except the pH of buffer A was titrated to 4.22, and the gradient table listed below:

TABLE 9

Gradient Table:

| Time(min) | Flow Rate(mL/min) | % A | % B | % C | Curve |
|---|---|---|---|---|---|
| Initial | 0.150 | 100 | 0 | 0 | Initial |
| 1.00 | 0.150 | 100 | 0 | 0 | 6 |
| 14.00 | 0.150 | 0 | 92 | 8 | 6 |
| 17.00 | 0.150 | 0 | 92 | 8 | 6 |
| 18.00 | 0.150 | 100 | 0 | 0 | 6 |
| 25.00 | 0.150 | 100 | 0 | 0 | 6 |

FIG. 11C presents chromatograms obtained with the buffer compositions listed for FIG. 11A except the pH of buffer A was titrated to 5.00, and the gradient table listed below:

TABLE 10

Gradient Table:

| Time(min) | Flow Rate(mL/min) | % A | % B | % C | Curve |
|---|---|---|---|---|---|
| Initial | 0.150 | 100 | 0 | 0 | Initial |
| 1.00 | 0.150 | 100 | 0 | 0 | 6 |
| 12.30 | 0.150 | 0 | 92 | 8 | 6 |
| 15.30 | 0.150 | 0 | 92 | 8 | 6 |
| 16.30 | 0.150 | 100 | 0 | 0 | 6 |
| 20.00 | 0.150 | 100 | 0 | 0 | 6 |

FIG. 11D presents chromatograms obtained with the buffer compositions listed for FIG. 11A except the pH of buffer A was titrated to 5.22, and the gradient table listed below:

TABLE 11

Gradient Table:

| Time(min) | Flow Rate(mLmin) | % A | % B | % C | Curve |
|---|---|---|---|---|---|
| Initial | 0.150 | 100 | 0 | 0 | Initial |
| 1.00 | 0.150 | 100 | 0 | 0 | 6 |
| 11.80 | 0.150 | 0 | 92 | 8 | 6 |
| 14.80 | 0.150 | 0 | 92 | 8 | 6 |
| 15.80 | 0.150 | 100 | 0 | 0 | 6 |
| 20.00 | 0.150 | 100 | 0 | 0 | 6 |

FIG. 11E presents chromatograms obtained with the buffer compositions listed for FIG. 11A except the pH of buffer A was titrated to 5.49, and the gradient table listed below:

TABLE 12

Gradient Table:

| Time(min) | Flow Rate(mL/min) | % A | % B | % C | Curve |
|---|---|---|---|---|---|
| Initial | 0.150 | 100 | 0 | 0 | Initial |
| 1.00 | 0.150 | 100 | 0 | 0 | 6 |
| 11.20 | 0.150 | 0 | 92 | 8 | 6 |
| 14.20 | 0.150 | 0 | 92 | 8 | 6 |
| 15.20 | 0.150 | 100 | 0 | 0 | 6 |
| 20.00 | 0.150 | 100 | 0 | 0 | 6 |

FIG. 13A presents chromatograms obtained with the buffer compositions, LC conditions, and gradient table listed below:

TABLE 13

Buffer Compositions:

| mM | succinic acid | Bis-Tris Propane | TEA | CAPSO | NaCl | pH |
|---|---|---|---|---|---|---|
| Buffer A | 10.5 | 8.3 | 9.0 | 6.0 | 0 | 4.99 |
| Buffer B | 10.5 | 8.3 | 9.0 | 6.0 | 0 | 10.21 |
| Buffer C | 0 | 0 | 0 | 0 | 500 | not adjusted |

TABLE 14

LC Conditions

| | |
|---|---|
| System | ACQUITY UPLC H-Class Bio |
| Column Stationary Phase: | 3 μm non-porous sulfonated strong cation exchange stationary phase |
| Column Dimension | 2.1 × 50 mm |
| Sample: | Dilute panitumumab, infliximab, trastuzumab, adalimumab, and NIST mAb with 18.2 MΩ purified water to concentrations of 5 mg/mL |
| Flow Rate: | 0.15 mL/min |
| Column Temperature: | 30° C. |
| Injection Volume: | 1 μL |
| Detection: | 280 nm |

TABLE 15

Gradient Table:

| Time(min) | Flow Rate(mL/min) | % A | % B | % C | Curve |
|---|---|---|---|---|---|
| Initial | 0.150 | 100 | 0 | 0 | Initial |
| 1.00 | 0.150 | 100 | 0 | 0 | 6 |
| 12.30 | 0.150 | 0 | 92 | 8 | 6 |
| 15.30 | 0.150 | 0 | 92 | 8 | 6 |
| 16.30 | 0.150 | 100 | 0 | 0 | 6 |
| 25.00 | 0.150 | 100 | 0 | 0 | 6 |

FIG. 13B presents chromatograms obtained with the LC conditions and gradient table listed for FIG. 13A, and the buffer compositions listed below:

TABLE 16

Buffer Compositions:

| mM | Succinic Acid | BIS-TRIS Propane | TEA | CAPSO | NaCl | pH |
|---|---|---|---|---|---|---|
| Buffer A | 10.5 | 6.0 | 9.0 | 6.0 | 0 | 5.00 |
| Buffer B | 10.5 | 6.0 | 9.0 | 6.0 | 0 | 10.21 |
| Buffer C | 0 | 0 | 0 | 0 | 500 | not adjusted |

FIG. 13C presents chromatograms obtained with the LC conditions and gradient table listed for FIG. 13A, and the buffer compositions listed below:

TABLE 17

Buffer Compositions:

| mM | Succinic Acid | BIS-TRIS Propane | TEA | CAPSO | NaCl | pH |
|---|---|---|---|---|---|---|
| Buffer A | 10.5 | 10.5 | 9.0 | 6.0 | 0 | 5.00 |
| Buffer B | 10.5 | 10.5 | 9.0 | 6.0 | 0 | 10.20 |
| Buffer C | 0 | 0 | 0 | 0 | 500 | not adjusted |

FIG. 13D presents chromatograms obtained with the LC conditions and gradient table listed for FIG. 13A, and the buffer compositions listed below:

TABLE 18

Buffer Compositions:

| mM | Succinic Acid | BIS-TRIS Propane | TEA | CAPSO | NaCl | pH |
|---|---|---|---|---|---|---|
| Buffer A | 10.5 | 8.3 | 9.0 | 4.0 | 0 | 4.99 |
| Buffer B | 10.5 | 8.3 | 9.0 | 4.0 | 0 | 10.22 |
| Buffer C | 0 | 0 | 0 | 0 | 500 | not adjusted |

FIG. 13E presents chromatograms obtained with the LC conditions and gradient table listed for FIG. 13A, and the buffer compositions listed below:

TABLE 19

Buffer Compositions:

| mM | Succinic Acid | BIS-TRIS Propane | TEA | CAPSO | NaCl | pH |
|---|---|---|---|---|---|---|
| Buffer A | 10.5 | 8.3 | 9.0 | 8.0 | 0 | 4.99 |
| Buffer B | 10.5 | 8.3 | 9.0 | 8.0 | 0 | 10.20 |
| Buffer C | 0 | 0 | 0 | 0 | 500 | not adjusted |

FIG. 13F presents chromatograms obtained with the LC conditions and gradient table listed for FIG. 13A, and the buffer compositions listed below:

TABLE 20

Buffer Compositions:

| mM | Succinic Acid | BIS-TRIS Propane | TEA | CAPSO | NaCl | pH |
|---|---|---|---|---|---|---|
| Buffer A | 10.5 | 8.3 | 11.0 | 6.0 | 0 | 5.00 |
| Buffer B | 10.5 | 8.3 | 11.0 | 6.0 | 0 | 10.20 |
| Buffer C | 0 | 0 | 0 | 0 | 500 | not adjusted |

FIG. 13G presents chromatograms obtained with the LC conditions and gradient table listed for FIG. 13A, and the buffer compositions listed below:

TABLE 21

Buffer Compositions:

| mM | Succinic Acid | BIS-TRIS Propane | TEA | CAPSO | NaCl | pH |
|---|---|---|---|---|---|---|
| Buffer A | 10.5 | 8.3 | 7.0 | 6.0 | 0 | 5.00 |
| Buffer B | 10.5 | 8.3 | 7.0 | 6.0 | 0 | 10.21 |
| Buffer C | 0 | 0 | 0 | 0 | 500 | not adjusted |

FIGS. 13H and 14A present chromatograms obtained with the buffer compositions, LC conditions, and gradient table listed below:

TABLE 22

Buffer Compositions:

| mM | Succinic Acid | BIS-TRIS Propane | TEA | CAPSO | NaCl | pH |
|---|---|---|---|---|---|---|
| Buffer A | 10.5 | 11.0 | 9.0 | 11.0 | 0 | 5.00 |
| Buffer B | 10.5 | 11.0 | 9.0 | 11.0 | 0 | 10.20 |
| Buffer C | 0 | 0 | 0 | 0 | 500 | not adjusted |
| Buffer D | | | Milli-Q water | | | |

TABLE 23A

LC Conditions

| | |
|---|---|
| System | ACQUITY UPLC H-Class Bio |
| Column Stationary Phase: | 3 µm non-porous sulfonated strong cation exchange stationary phase |
| Column Dimension | 2.1 × 50 mm |
| Sample: | Dilute panitumumab, infliximab, trastuzumab, adalimumab, and NIST mAb with 18.2 MΩ purified water to concentrations of 5 mg/mL |
| Flow Rate: | 0.15 mL/min |
| Column Temperature: | 30° C. |
| Injection Volume: | 1 µL |
| Detection: | 280 nm |

TABLE 23B

Gradient Table:

| Time (min) | Flow Rate (mL/min) | % A | % B | % C | % D | Curve |
|---|---|---|---|---|---|---|
| Initial | 0.150 | 100 | 0 | 0 | 0 | Initial |
| 1.00 | 0.150 | 100 | 0 | 0 | 0 | 6 |
| 12.30 | 0.150 | 0 | 92 | 8 | 0 | 6 |
| 15.30 | 0.150 | 0 | 92 | 8 | 0 | 6 |
| 16.30 | 0.150 | 100 | 0 | 0 | 0 | 6 |
| 25.00 | 0.150 | 100 | 0 | 0 | 0 | 6 |

FIG. 14B presents chromatograms obtained with the LC conditions and gradient table listed for FIG. 14A, and the buffer compositions listed below:

TABLE 24

Gradient Table:

| Time (min) | Flow Rate (mL/min) | % A | % B | % C | % D | Curve |
|---|---|---|---|---|---|---|
| Initial | 0.150 | 90 | 0 | 0 | 10 | Initial |
| 1.00 | 0.150 | 90 | 0 | 0 | 10 | 6 |
| 12.30 | 0.150 | 0 | 92 | 8 | 0 | 6 |
| 15.30 | 0.150 | 0 | 92 | 8 | 0 | 6 |
| 16.30 | 0.150 | 90 | 0 | 0 | 10 | 6 |
| 25.00 | 0.150 | 90 | 0 | 0 | 10 | 6 |

Example 2. Ion Exchange Chromatography with Buffers Composed of Histidine and Gly-Gly FIG. 3A presents chromatograms obtained with the buffer compositions, LC conditions, and gradient table listed below:

TABLE 25

Buffer Compositions:

| mM | Histidine | Gly-Gly | NaCl | pH |
|---|---|---|---|---|
| Buffer A | 20.0 | 11.5 | 0 | 5.39 |
| Buffer B | 20.0 | 11.5 | 0 | 10.42 |
| Buffer C | 0 | 0 | 500 | not adjusted |

TABLE 26

Gradient Table:

| Time(min) | Flow Rate(mL/min) | % A | % B | % C | Curve |
|---|---|---|---|---|---|
| Initial | 0.150 | 100 | 0 | 0 | Initial |
| 1.00 | 0.150 | 100 | 0 | 0 | 6 |
| 11.80 | 0.150 | 0 | 92 | 8 | 6 |
| 14.80 | 0.150 | 0 | 92 | 8 | 6 |
| 15.80 | 0.150 | 100 | 0 | 0 | 6 |
| 20.00 | 0.150 | 100 | 0 | 0 | 6 |

Example 3. Ion Exchange Chromatography with Buffers Composed of Glycine, Citric Acid, and Gly-Gly FIG. 3B presents chromatograms obtained with the buffer compositions, LC conditions, and gradient table listed below:

TABLE 27

Buffer Compositions:

| mM | Glycine | Citric acid | Gly-Gly | NaCl | pH |
|---|---|---|---|---|---|
| Buffer A | 10.0 | 10.0 | 11.0 | 0 | 5.20 |
| Buffer B | 10.0 | 10.0 | 11.0 | 0 | 10.41 |

TABLE 28

LC Conditions

| System | ACQUITY UPLC H-Class Bio |
|---|---|
| Column Stationary Phase: | 3 µm non-porous sulfonated strong cation exchange stationary phase |
| Column Dimension | 2.1 × 50 mm |
| Sample: | Dilute panitumumab, infliximab, trastuzumab, adalimumab, and NIST mAb with 18.2 MΩ purified water to concentrations of 5 mg/mL |
| Flow Rate: | 0.15 mL/min |
| Column Temperature: | 30° C. |
| Injection Volume: | 1 µL |
| Detection: | 280 nm |

TABLE 29

Gradient Table:

| Time(min) | Flow Rate(mL/min) | % A | % B | Curve |
|---|---|---|---|---|
| Initial | 0.150 | 100 | 0 | Initial |
| 1.00 | 0.150 | 100 | 0 | 6 |
| 12.30 | 0.150 | 0 | 100 | 6 |
| 15.30 | 0.150 | 0 | 100 | 6 |
| 16.30 | 0.150 | 100 | 0 | 6 |
| 20.00 | 0.150 | 100 | 0 | 6 |

Example 4. Ion Exchange Chromatography with Buffers Composed of Glycine, MES, and Gly-Gly FIG. 3C presents chromatograms obtained with the buffer compositions, LC conditions, and gradient table listed below:

TABLE 30

Buffer Compositions:

| mM | Glycine | MES | Gly-Gly | NaCl | pH |
|---|---|---|---|---|---|
| Buffer A | 10.0 | 12.0 | 11.0 | 0 | 5.45 |
| Buffer B | 10.0 | 12.0 | 11.0 | 0 | 10.41 |
| Buffer C | 0 | 0 | 0 | 500 | not adjusted |

TABLE 31

LC Conditions

| System | ACQUITY UPLC H-Class Bio |
|---|---|
| Column Stationary Phase: | 3 µm non-porous sulfonated strong cation exchange stationary phase |
| Column Dimension | 2.1 × 50 mm |
| Sample: | Dilute panitumumab, infliximab, trastuzumab, adalimumab, and NIST mAb with 18.2 MΩ purified water to concentrations of 5 mg/mL |
| Flow Rate: | 0.15 mL/min |
| Column Temperature: | 30° C. |
| Injection Volume: | 1 µL |
| Detection: | 280 nm |

TABLE 32

Gradient Table:

| Time (min) | Flow Rate (mL/min) | % A | % B | % C | Curve |
|---|---|---|---|---|---|
| Initial | 0.150 | 100 | 0 | 0 | Initial |
| 1.00 | 0.150 | 100 | 0 | 0 | 6 |
| 11.80 | 0.150 | 0 | 98 | 2 | 6 |
| 14.80 | 0.150 | 0 | 98 | 2 | 6 |
| 15.80 | 0.150 | 100 | 0 | 0 | 6 |
| 20.00 | 0.150 | 100 | 0 | 0 | 6 |

Example 5. Ion Exchange Chromatography with Buffers Composed of Succinic Acid, ACES, 2-Amino-2-methyl-1,3-propanediol (AMPD), TEA, and CAPS FIG. 4A presents chromatograms obtained with the buffer compositions, LC conditions, and gradient table listed below:

TABLE 33

Buffer Compositions:

| mM | Succinic Acid | ACES | AMPD | TEA | CAPS | NaCl | pH |
|---|---|---|---|---|---|---|---|
| Buffer A | 5.5 | 4.5 | 5.5 | 3.0 | 4.5 | 0 | 3.49 |
| Buffer B | 5.5 | 4.5 | 5.5 | 3.0 | 4.5 | 0 | 11.00 |
| Buffer C | 0 | 0 | 0 | 0 | 0 | 500 | not adjusted |

TABLE 34

LC Conditions

| | |
|---|---|
| System | ACQUITY UPLC H-Class Bio |
| Column Stationary Phase: | 3 µm non-porous sulfonated strong cation exchange stationary phase |
| Column Dimension | 2.1 × 50 mm |
| Sample: | Dilute panitumumab, infliximab, trastuzumab, adalimumab, and NIST mAb with 18.2 MΩ purified water to concentrations of 5 mg/mL |
| Flow Rate: | 0.15 mL/min |
| Column Temperature: | 30° C. |
| Injection Volume: | 1 µL |
| Detection: | 280 nm |

TABLE 35

Gradient Table:

| Time (min) | Flow Rate (mL/min) | % A | % B | % C | Curve |
|---|---|---|---|---|---|
| Initial | 0.150 | 100 | 0 | 0 | Initial |
| 1.00 | 0.150 | 100 | 0 | 0 | 6 |
| 17.30 | 0.150 | 0 | 92 | 8 | 6 |
| 20.30 | 0.150 | 0 | 92 | 8 | 6 |
| 21.30 | 0.150 | 100 | 0 | 0 | 6 |
| 30.00 | 0.150 | 100 | 0 | 0 | 6 |

Example 6. Ion Exchange Chromatography with Buffers Composed of Succinic Acid, BIS-TRIS Propane, TEA, and CAPS FIGS. 4B and 6A presents chromatograms obtained with the buffer compositions, LC conditions, and gradient table listed below:

TABLE 36

Buffer Compositions:

| mM | Succinic Acid | BIS-TRIS Propane | TEA | CAPS | NaCl | pH |
|---|---|---|---|---|---|---|
| Buffer A | 10.0 | 10.0 | 10.0 | 14.0 | 0 | 3.50 |
| Buffer B | 10.0 | 12.0 | 10.0 | 10.0 | 0 | 11.01 |
| Buffer C | 0 | 0 | 0 | 0 | 500 | not adjusted |
| Buffer D | 18.2 MΩ purified water | | | | | |

TABLE 37

LC Conditions

| | |
|---|---|
| System | ACQUITY UPLC H-Class Bio |
| Column Stationary Phase: | 3 µm non-porous sulfonated strong cation exchange stationary phase |
| Column Dimension | 2.1 × 50 mm |
| Sample: | Dilute panitumumab, infliximab, trastuzumab, adalimumab, and NIST mAb with 18.2 MΩ purified water to concentrations of 5 mg/mL |

TABLE 37-continued

LC Conditions

| | |
|---|---|
| Flow Rate: | 0.15 mL/min |
| Column Temperature: | 30° C. |
| Injection Volume: | 1 µL |
| Detection: | 280 nm |

TABLE 38

Gradient Table:

| Time (min) | Flow Rate (mL/min) | % A | % B | % C | % D | Curve |
|---|---|---|---|---|---|---|
| Initial | 0.150 | 75 | 0 | 0 | 25 | Initial |
| 1.00 | 0.150 | 75 | 0 | 0 | 25 | 6 |
| 17.30 | 0.150 | 0 | 68 | 7 | 25 | 6 |
| 20.30 | 0.150 | 0 | 68 | 7 | 25 | 6 |
| 21.30 | 0.150 | 75 | 0 | 0 | 25 | 6 |
| 30.00 | 0.150 | 75 | 0 | 0 | 25 | 6 |

FIGS. 5B and 9B present chromatograms obtained with the buffer compositions and LC conditions listed for FIG. 4B, and the gradient table listed below:

TABLE 39

Gradient Table:

| Time (min) | Flow Rate (mL/min) | % A | % B | % C | % D | Curve |
|---|---|---|---|---|---|---|
| Initial | 0.150 | 75 | 0 | 0 | 25 | Initial |
| 1.00 | 0.150 | 75 | 0 | 0 | 25 | 6 |
| 11.00 | 0.150 | 0 | 67 | 8 | 25 | 6 |
| 14.00 | 0.150 | 0 | 67 | 8 | 25 | 6 |
| 15.00 | 0.150 | 75 | 0 | 0 | 25 | 6 |
| 20.00 | 0.150 | 75 | 0 | 0 | 25 | 6 |

Example 7. Ion Exchange Chromatography with Buffers Composed of Succinic Acid, BIS-TRIS propane, TEA, and AMP FIG. 5A presents chromatograms obtained with the buffer compositions, LC conditions, and gradient table listed below:

TABLE 40

Buffer Compositions:

| mM | Succinic Acid | BIS-TRIS Propane | TEA | AMP | NaCl | pH |
|---|---|---|---|---|---|---|
| Buffer A | 13.0 | 10.0 | 10.0 | 10.0 | 0 | 3.53 |
| Buffer B | 13.0 | 10.0 | 10.0 | 10.0 | 0 | 11.01 |
| Buffer C | 0 | 0 | 0 | 0 | 500 | not adjusted |
| Buffer D | 18.2 MΩ purified water | | | | | |

TABLE 41

| | LC Conditions |
|---|---|
| System | ACQUITY UPLC H-Class Bio |
| Column Stationary Phase: | 3 µm non-porous sulfonated strong cation exchange stationary phase |
| Column Dimension | 2.1 × 50 mm |
| Sample: | Dilute panitumumab, infliximab, trastuzumab, adalimumab, and NIST mAb with 18.2 MΩ purified water to concentrations of 5 mg/mL |
| Flow Rate: | 0.15 mL/min |
| Column Temperature: | 30° C. |
| Injection Volume: | 1 µL |
| Detection: | 280 nm |

TABLE 42

Gradient Table:

| Time (min) | Flow Rate (mL/min) | % A | % B | % C | % D | Curve |
|---|---|---|---|---|---|---|
| Initial | 0.150 | 75 | 0 | 0 | 25 | Initial |
| 1.00 | 0.150 | 75 | 0 | 0 | 25 | 6 |
| 11.00 | 0.150 | 0 | 69 | 6 | 25 | 6 |
| 14.00 | 0.150 | 0 | 69 | 6 | 25 | 6 |
| 15.00 | 0.150 | 75 | 0 | 0 | 25 | 6 |
| 20.00 | 0.150 | 75 | 0 | 0 | 25 | 6 |

Example 8. Ion Exchange Chromatography with Buffers Composed of Succinic Acid, BIS-TRIS propane, EPPS, and CAPSO FIG. 7A presents chromatograms obtained with the buffer compositions, LC conditions, and gradient table listed below:

TABLE 43

Buffer Compositions:

| mM | Succinic Acid | BIS-TRIS Propane | EPPS | CAPSO | NaCl | pH |
|---|---|---|---|---|---|---|
| Buffer A | 14.0 | 12.0 | 10.0 | 6.0 | 0 | 4.00 |
| Buffer B | 14.0 | 12.0 | 10.0 | 6.0 | 0 | 10.21 |
| Buffer C | 0 | 0 | 0 | 0 | 500 | not adjusted |

TABLE 44

| | LC Conditions |
|---|---|
| System | ACQUITY UPLC H-Class Bio |
| Column Stationary Phase: | 3 µm non-porous sulfonated strong cation exchange stationary phase |
| Column Dimension | 2.1 × 50 mm |
| Sample: | Dilute panitumumab, infliximab, trastuzumab, adalimumab, and NIST mAb with 18.2 MΩ purified water to concentrations of 5 mg/mL |
| Flow Rate: | 0.15 mL/min |
| Column Temperature: | 30° C. |
| Injection Volume: | 1 µL |
| Detection: | 280 nm |

TABLE 45

Gradient Table:

| Time (min) | Flow Rate (mL/min) | % A | % B | % C | Curve |
|---|---|---|---|---|---|
| Initial | 0.150 | 100 | 0 | 0 | Initial |
| 1.00 | 0.150 | 100 | 0 | 0 | 6 |
| 14.50 | 0.150 | 0 | 92 | 8 | 6 |
| 17.50 | 0.150 | 0 | 92 | 8 | 6 |
| 18.50 | 0.150 | 100 | 0 | 0 | 6 |
| 25.00 | 0.150 | 100 | 0 | 0 | 6 |

Example 9. Ion Exchange Chromatography with Buffers Composed of MES, BIS-TRIS Propane, TEA, and CAPSO FIG. 8A present chromatograms obtained with the buffer compositions, LC conditions, and gradient table listed below:

TABLE 46

Buffer Compositions:

| mM | MES | BIS-TRIS Propane | TEA | CAPSO | NaCl | pH |
|---|---|---|---|---|---|---|
| Buffer A | 9.0 | 9.9 | 8.1 | 9.9 | 0 | 5.59 |
| Buffer B | 10.0 | 11.0 | 9.0 | 11.0 | 40.0 | 10.22 |

TABLE 47

| | LC Conditions |
|---|---|
| System | ACQUITY UPLC H-Class Bio |
| Column Stationary Phase: | 3 µm non-porous sulfonated strong cation exchange stationary phase |
| Column Dimension | 4.6 × 50 mm |
| Sample: | Dilute panitumumab, infliximab, trastuzumab, adalimumab, and NIST mAb with 18.2 MΩ purified water to concentrations of 5 mg/mL |
| Flow Rate: | 0.72 mL/min |
| Column Temperature: | 30° C. |
| Injection Volume: | 5 µL |
| Detection: | 280 nm |

TABLE 48

Gradient Table:

| Time (min) | Flow Rate (mL/min) | % A | % B | Curve |
|---|---|---|---|---|
| Initial | 0.720 | 100 | 0 | Initial |
| 1.00 | 0.720 | 100 | 0 | 6 |
| 11.00 | 0.720 | 0 | 100 | 6 |
| 14.00 | 0.720 | 0 | 100 | 6 |
| 15.00 | 0.720 | 100 | 0 | 6 |
| 20.00 | 0.720 | 100 | 0 | 6 |

Example 10. Ion Exchange Chromatography with Buffers Composed of Succinic Acid, BIS-TRIS Propane, TEA, and β-alanine FIG. 9A presents chromatograms obtained with the buffer compositions, LC conditions, and gradient table listed below:

TABLE 49

| | Buffer Compositions: | | | | | |
|---|---|---|---|---|---|---|
| mM | Succinic Acid | BIS-TRIS Propane | TEA | β-alanine | NaCl | pH |
| Buffer A | 9.0 | 11.0 | 10.0 | 9.0 | 0 | 3.51 |
| Buffer B | 9.0 | 11.0 | 10.0 | 9.0 | 0 | 11.01 |
| Buffer C | 0 | 0 | 0 | 0 | 500 | not adjusted |
| Buffer D | 18.2 MΩ purified water | | | | | |

TABLE 50

| LC Conditions | |
|---|---|
| System | ACQUITY UPLC H-Class Bio |
| Column Stationary Phase: | 3 µm non-porous sulfonated strong cation exchange stationary phase |
| Column Dimension | 2.1 × 50 mm |
| Sample: | Dilute panitumumab, infliximab, trastuzumab, adalimumab, and NIST mAb with 18.2 MΩ purified water to concentrations of 5 mg/mL |
| Flow Rate: | 0.15 mL/min |
| Column Temperature: | 30° C. |
| Injection Volume: | 1 µL |
| Detection: | 280 nm |

TABLE 51

| Gradient Table: | | | | | | |
|---|---|---|---|---|---|---|
| Time (min) | Flow Rate (mL/min) | % A | % B | % C | % D | Curve |
| Initial | 0.150 | 75 | 0 | 0 | 25 | Initial |
| 1.00 | 0.150 | 75 | 0 | 0 | 25 | 6 |
| 11.00 | 0.150 | 0 | 67 | 8 | 25 | 6 |
| 14.00 | 0.150 | 0 | 67 | 8 | 25 | 6 |
| 15.00 | 0.150 | 75 | 0 | 0 | 25 | 6 |
| 20.00 | 0.150 | 75 | 0 | 0 | 25 | 6 |

Example 11. Ion Exchange Chromatography with Buffers Composed of Piperazine, Imidazole, and TRIS FIG. 15A presents chromatograms obtained with the buffer compositions, LC conditions, and gradient table listed below:

TABLE 52

| | Buffer Compositions: | | | | |
|---|---|---|---|---|---|
| mM | Piperazine | Imidazole | TRIS | NaCl | pH |
| Buffer A | 4.0 | 4.0 | 4.0 | 0 | 5.05 |
| Buffer B | 4.0 | 4.0 | 4.0 | 0 | 10.76 |
| Buffer C | 0 | 0 | 0 | 500 | not adjusted |

TABLE 53

| LC Conditions | |
|---|---|
| System | ACQUITY UPLC H-Class Bio |
| Column Stationary Phase: | 3 µm non-porous sulfonated strong cation exchange stationary phase |
| Column Dimension | 4.6 × 50 mm |
| Sample: | Dilute panitumumab, infliximab, trastuzumab, adalimumab, and NIST mAb with 18.2 MΩ purified water to concentrations of 5 mg/mL |
| Flow Rate: | 0.72 mL/min |
| Column Temperature: | 30° C. |
| Injection Volume: | 5 µL |
| Detection: | 280 nm |

TABLE 54

| Gradient Table: | | | | | |
|---|---|---|---|---|---|
| Time (min) | Flow Rate (mL/min) | % A | % B | % C | Curve |
| Initial | 0.720 | 100 | 0 | 0 | Initial |
| 1.00 | 0.720 | 100 | 0 | 0 | 6 |
| 26.20 | 0.720 | 0 | 96.8 | 3.2 | 6 |
| 29.20 | 0.720 | 0 | 96.8 | 3.2 | 6 |
| 30.20 | 0.720 | 100 | 0 | 0 | 6 |
| 45.00 | 0.720 | 100 | 0 | 0 | 6 |

Example 12. Ion Exchange Chromatography with Thermo CX-1 pH Gradient Buffers

FIG. 15B presents chromatograms obtained with the LC conditions and gradient table listed below:

TABLE 55

| LC Conditions | |
|---|---|
| System | ACQUITY UPLC H-Class Bio |
| Column Stationary Phase: | 3 µm non-porous sulfonated strong cation exchange stationary phase |
| Column Dimension | 4.6 × 50 mm |
| Sample: | Dilute panitumumab, infliximab, trastuzumab, adalimumab, and NIST mAb with 18.2 MΩ purified water to concentrations of 5 mg/mL |
| Flow Rate: | 0.72 mL/min |
| Column Temperature: | 30° C. |
| Injection Volume: | 5 µL |
| Detection: | 280 nm |

TABLE 56

| Gradient Table: | | | | |
|---|---|---|---|---|
| Time (min) | Flow Rate (mL/min) | % A | % B | Curve |
| Initial | 0.720 | 100 | 0 | Initial |
| 1.00 | 0.720 | 100 | 0 | 6 |
| 21.00 | 0.720 | 0 | 100 | 6 |
| 24.00 | 0.720 | 0 | 100 | 6 |
| 25.00 | 0.720 | 100 | 0 | 6 |
| 30.00 | 0.720 | 100 | 0 | 6 |

The invention claimed is:

1. A chromatographic elution buffer solution comprising a plurality of buffer salts, the buffer solution having a first pKa value that ranges from 4.5 to 6.5, a second pKa value that ranges from 6.5 to 7.5, a third pKa value that ranges from 7.5 to 8.5, a fourth pKa value that ranges from 8.5 to 9.5, and a fifth pKa value that ranges from 9.5 to 11.

2. The chromatographic elution buffer solution of claim 1, wherein the buffer solution has a pH ranging from 3 to 11.

3. Chromatographic elution buffer solution of claim 1, wherein the first pKa value is provided by a first buffer salt that is a diprotic acid, (b) wherein the second pKa value and the fourth pKa value are provided by a second buffer salt that is a divalent buffer salt with two amine groups, (c) wherein the third pKa is provided by a third buffer salt that is a monovalent buffer salt comprising a single amine group, and (d) wherein the fifth pKa value is provided by a fourth buffer salt that is a zwitterionic buffer salt.

4. The chromatographic elution buffer solution of claim 3, comprising a single zwitterionic buffer salt.

5. The chromatographic elution buffer of claim 3, wherein the diprotic acid buffer salt is succinic acid.

6. The chromatographic elution buffer of claim 3, wherein the divalent buffer salt is BIS-TRIS propane.

7. The chromatographic elution buffer of claim 3, wherein the monovalent buffer salt is selected from the group consisting of triethanolamine and TRIS.

8. The chromatographic elution buffer of claim 3, wherein the zwitterionic buffer salt is selected from the group consisting of zwitterionic buffer salt comprising a sulfonate group and an amine group and a zwitterionic buffer salt comprising a carboxyl group and an amine group.

9. The chromatographic elution buffer of claim 3, wherein the zwitterionic buffer salt is selected from the group consisting of CAPSO, CAPS and β-alanine.

10. A chromatographic elution buffer kit comprising (a) a first buffer solution comprising a chromatographic elution buffer solution comprising a plurality of buffer salts, the buffer solution having a first pKa value that ranges from 4.5 to 6.5, a second pKa value that ranges from 6.5 to 7.5, a third pKa value that ranges from 7.5 to 8.5, a fourth pKa value that ranges from 8.5 to 9.5, and a fifth pKa value that ranges from 9.5 to 11, wherein the buffer solution has a pH ranging from 3 to 7 or has a pH ranging from 3 to 7 upon dilution with water in a ratio ranging from 1:2 to 1:20 and (b) a second buffer solution comprising a chromatographic elution buffer solution comprising a plurality of buffer salts, the buffer solution having a first pKa value that ranges from 4.5 to 6.5, a second pKa value that ranges from 6.5 to 7.5, a third pKa value that ranges from 7.5 to 8.5, a fourth pKa value that ranges from 8.5 to 9.5, and a fifth pKa value that ranges from 9.5 to 11, wherein the second buffer solution has a pH ranging from 9 to 11 or has a pH ranging from 9 to 11 upon dilution with water in a ratio ranging from 1:2 to 1:20, wherein the second buffer solution comprises a non-buffer salt.

11. The chromatographic elution buffer kit of claim 10, wherein each of the first, second, third and fourth buffer salts is present in the first buffer solution at a concentration ranging from 2 to 20 millimolar and/or wherein each of the first, second, third and fourth buffer salts is present in the second buffer solution at a concentration ranging from 2 to 20 millimolar.

12. The chromatographic elution buffer kit of claim 10, wherein the non-buffer salt comprises (a) a cation selected from the group consisting of alkali metal cations, alkaline earth metal cations, transition metal cations, ammonium cations and (b) an anion selected from the group consisting of halide anions, nitrate anions, sulfate anions, phosphate anions, carbonate anions, chlorate anions, thiocyanate anions and perchlorate anions.

13. The chromatographic elution buffer kit of claim 12, wherein the concentration of the non-buffer salt ranges from 1 to 100 millimolar.

14. The chromatographic elution buffer kit of claim 10, wherein a concentration of each of the first, second, third and fourth buffer salts in the first buffer solution is from 10% to 30% lower than a concentration of each of the first, second, third and fourth buffer salts in the second buffer solution.

15. The chromatographic elution buffer kit of claim 10, wherein a total concentration of the first, second, third and fourth buffer salts in the first buffer solution is from 10% to 30% lower than a total concentration of the first, second, third and fourth buffer salts in the second buffer solution.

16. The chromatographic elution buffer kit of claim 10, wherein a plot of pH versus volume percent of the first buffer solution relative to a total volume for a binary mixture of the first buffer solution and the second buffer solution is linear.

17. The chromatographic elution buffer kit of claim 10, wherein a plot of conductivity versus volume percent of the first buffer solution relative to a total volume for a binary mixture of the first buffer solution and the second buffer solution is linear.

18. The chromatographic elution buffer kit of claim 10, wherein a plot of conductivity versus volume percent of the first buffer solution relative to a total volume for a binary mixture of the first buffer solution and the second buffer solution does not exhibit a negative slope.

19. The chromatographic elution buffer kit of claim 10, wherein the first buffer solution has a conductivity ranging from 0.5 millisiemens (mS) to 3 mS and wherein the second buffer solution has a conductivity ranging from 3 mS to 100 mS.

20. The chromatographic elution buffer kit of claim 10, further comprising an ion-exchange chromatography material.

21. The chromatographic elution buffer kit of claim 20, comprising a separation device comprising a housing comprising an inlet and an outlet, wherein the ion-exchange chromatography material is housed in the housing.

22. The chromatographic elution buffer kit of claim 20, wherein the ion-exchange chromatography material is a cation exchange chromatography material.

23. The chromatographic elution buffer kit of claim 22, wherein the cation exchange chromatography material comprises carboxylate groups.

24. The chromatographic elution buffer kit of claim 22, wherein the cation exchange chromatography material comprises sulfonate groups.

25. A method for analyzing a sample comprising a plurality of analytes, the method comprising:
  loading the sample onto an ion-exchange chromatography material thereby binding the plurality of analytes to the ion-exchange chromatography material and
  eluting the plurality of analytes from the ion-exchange chromatography material with a mobile phase comprising a chromatographic elution buffer solution comprising a plurality of buffer salts, the buffer solution having a first pKa value that ranges from 4.5 to 6.5, a second pKa value that ranges from 6.5 to 7.5, a third pKa value that ranges from 7.5 to 8.5, a fourth pKa value that ranges from 8.5 to 9.5, and a fifth pKa value that ranges from 9.5 to 11, thereby separating at least some of the plurality of analytes.

* * * * *